(12) United States Patent
Lopez et al.

(10) Patent No.: US 11,925,645 B2
(45) Date of Patent: *Mar. 12, 2024

(54) ENHANCED CAFFEINATED BEVERAGE COMPOSITION

(71) Applicant: Ortho-Nutra, LLC, Morganville, NJ (US)

(72) Inventors: Hector L. Lopez, Cream Ridge, NJ (US); Tim N. Ziegenfuss, Chardon, OH (US); Matthew Titlow, Carlsbad, CA (US)

(73) Assignee: ORTHO-NUTRA, LLC, Morganville, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/172,021

(22) Filed: Feb. 21, 2023

(65) Prior Publication Data

US 2023/0190757 A1 Jun. 22, 2023

Related U.S. Application Data

(63) Continuation of application No. 17/084,777, filed on Oct. 30, 2020, now Pat. No. 11,583,534, which is a continuation-in-part of application No. 16/551,373, filed on Aug. 26, 2019, now Pat. No. 11,426,410, which is a continuation of application No. 15/600,371, filed on May 19, 2017, now Pat. No. 10,398,701, which is a continuation-in-part of application No. 14/539,726, filed on Nov. 12, 2014, now Pat. No. 10,272,091.

(60) Provisional application No. 62/955,261, filed on Dec. 30, 2019, provisional application No. 61/903,362, filed on Nov. 12, 2013.

(51) Int. Cl.

| A61K 31/522 | (2006.01) |
| A23L 33/10 | (2016.01) |
| A23L 33/105 | (2016.01) |
| A61K 31/133 | (2006.01) |
| A61K 31/14 | (2006.01) |
| A61K 31/4748 | (2006.01) |
| A61K 31/685 | (2006.01) |
| A61K 31/7048 | (2006.01) |
| A61K 31/7068 | (2006.01) |
| C07D 487/04 | (2006.01) |

(52) U.S. Cl.
CPC .......... *A61K 31/522* (2013.01); *A23L 33/10* (2016.08); *A23L 33/105* (2016.08); *A61K 31/133* (2013.01); *A61K 31/14* (2013.01); *A61K 31/4748* (2013.01); *A61K 31/685* (2013.01); *A61K 31/7048* (2013.01); *A61K 31/7068* (2013.01); *C07D 487/04* (2013.01); *A23V 2002/00* (2013.01)

(58) Field of Classification Search
CPC .... A61K 31/522; A61K 31/133; A61K 31/14; A61K 31/4748; A61K 31/685; A61K 31/7048; A61K 31/7068; A23L 33/10; A23L 33/105; C07D 487/04; A23V 2002/00

See application file for complete search history.

(56) References Cited

U.S. PATENT DOCUMENTS

| 4,833,147 A | 5/1989 | Moeller et al. |
| 2015/0132280 A1 | 5/2015 | Lopez et al. |
| 2015/0238494 A1 | 8/2015 | Owoc |
| 2021/0137928 A1 | 5/2021 | Lopez et al. |

FOREIGN PATENT DOCUMENTS

| CN | 101289448 A | 10/2008 |
| WO | 2018/112475 A1 | 6/2018 |

OTHER PUBLICATIONS

Kuhman et al, "Cognitive Performance and Mood Following Ingestion of a Theacrine-Containing Dietary Supplement, Caffeine, or Placebo by Young Men and Women", Nutrients, vol. 7, Nov. 19, 2015, pp. 9618-9632.
Wanner et al, "O(2), 1,9-Trimethyluric Acid and 1,3,7,9-Tetramethyluric Acid in Leaves of Different Coffea Species" Phytochemistry, 1975, 14:747-750.
Li et al, "Antioxidative activities and the chemical constituents of two Chinese tease, Camellia kucha and C. ptilophylla", Intl. J. of Food Science and Tech, 2012, 47:1063-1071.
Feduccia et al, "Locomotor activation by theacrine, a purine alkaloid structurally similar to caffeine: Involvement of adenosine and dopamine receptors", Pharmacology, Biochemistry and Behavior, 2012, 102:241-248.
Petermann et al., "Metabolic Relations between Methylxanthines and Methyluric Acids in Coffea L.", Plant Physiol., 1983, 73:961-964.
Zheng et al, "Theacrine (1,3,7,9-tetramethyluric acid) synthesis in leaves of a Chinese tea, kucha (*Camellia assamica* var. kucha)", Phytochemistry, 2002, 60:129-134.
Li et al, "Theacrine, a Purine Alkaloid Obtained from Camellia assamica var. kucha, Attenuates Restraint Stress-Provoked Liver Damage in Mice", J. of Agricultural and Food Chem., 2013, 61:6328-6335.
Wang et al., "Theacrine, a purine alkaloid with anti-inflammatory and analgesic activities," Fitoterapia, 2010, 81:627-631.
Xu et al, "Theacrine, a special purine alkaloid with sedative and hypnotic properties from Cammelia assamica var. kucha in mice", J. of Asian Natural Products Research, 2007, vol. 9, No. 7, 665-672.
Xie et al., Chinese Pharmacological Bulletin, 2009, 9:13, Abstract Only.
Fisone et al., CMLS, Cell. Mol. Life Sci., 2004, vol. 61, p. 857-872.
Fox, K.R, Public Health Nutrition, 1999, vol. 2, No. 3a, p. 411-418.
Maridakis et al., International Journal of Neuroscience, 2009, vol. 119, p. 975-994.

(Continued)

*Primary Examiner* — Kade Ariani
(74) *Attorney, Agent, or Firm* — Umberg Zipser LLP

(57) ABSTRACT

An enhanced caffeinated beverage composition includes a caffeinated drink combined with an effective blend of methylliberine and theacrine providing increased mood, energy, alertness, focus, motivation, and/or decreased fatigue without adversely affecting heart rate or blood pressure.

20 Claims, 25 Drawing Sheets

(56) References Cited

OTHER PUBLICATIONS

Proceedings of the Eleventh International Society of Sports Nutrition (ISSN) Conference and Expo; Journal of the International Society of Sports Nutrition 2014, vol. 11 Suppl 1, published Dec. 1, 2014, 21 pages.

Lack of Drive? Theacrine will get you going dated May 19, 2012 and archived by the Internet Archive on Oct. 18, 2013.

Ye, Chuang-Xing, "New Discovery of Pattern of Purine Alkaloids in Wild Tea Trees," Acta Scientiarum Naturalium Universitatis Sunyatseni, Jan. 1, 2003, 42(1):62-65, Abstract only.

Theacrine Scientific Review on Usage Dosage Side Effects from Examine.com dated Nov. 20, 2013 and archived by the Internet Archive on Dec. 2, 2013.

PubChem compound summary for theobromine, downloaded on Nov. 20, 2018, 2 pages of PDF (cited in Notice of References Cited issued in parent U.S. Appl. No. 15/600,371).

PubChem compound summary for naringin, downloaded on Nov. 20, 2018, 3 pages of PDF (cited in Notice of References Cited issued in parent U.S. Appl. No. 15/600,371).

Grossman, R., Am J Clin Dermatol. 2005, vol. 6, No. 1, p. 39-47, Abstract Only (cited in Notice of References Cited issued in parent U.S. Appl. No. 15/600,371).

Kumar et al., Food Reviews International, 2009, vol. 25, p. 175-197 (cited in Notice of References Cited issued in parent U.S. Appl. No. 15/600,371).

Definition of synergism. (1992). In C. G. Morris (Ed.), Academic Press Dictionary of Science and Technology (4th ed.). Oxford, UK: Elsevier Science & Technology. Retrieved from https://search.credoreference.com/content/entry/apdst/synergism/0?institutionId=743 on Nov. 21, 2018, 1 page (cited in Notice of References Cited issued in parent U.S. Appl. No. 15/600,371).

International Searching Authority of the US Patent and Trademark Office, "International Search Report and Written Opinion" issued in related foreign patent application No. PCT/US2020/058138, dated Feb. 2, 2021, pp. 1-8.

Davis, JL, "Antioxidants in Green and Black Tea," Sep. 11, 2008. Retrieved from the Internet < URL: https://webmd.com/food-recipes/features/antioxidants-in-gree-and-black-tea#1> 6 pages.

Roberts, C, "Is There More Caffeine in Espresso Than in Coffee?" Nov. 13, 2018. Retrieved from the Internet < URL: https://www.consumerreports.org/coffee/is-there-more-caffeine-in-espresso-than-in-coffee/#:~text+By%20the%20Numbers,mg%20of%20caffeine%20per%20ounce.> 7 pages.

Lu et al., "Determination of purine alkaloids and catechins in different parts of Camellia assamica var. kucha by HPLC-DAD/ESI-MS/MS," Wiley Interscience, pp. 2024-2029 (Jul. 20, 2009).

Wang, D. et al., "Primary Studies on Acute Toxicity and Sedative/Hypnotic Activity of Camellia kucha" J. Sun Yat-San Univ. 49(1):76-79 (2010).

Satoshi Ikuta "Brain Use Manual Full Color Edition" Jilin Publishing Group p. 32 (2012) (cited as "common knowledge" document).

Sun, S. et al. "Food Toxicology" Wuhan University of Technology Press p. 170-173 (2012) (cited as "common knowledge" document).

Clarke, R.J., et al., Coffee, vol. 3; Physiology, Springer Science and Business Media, Dec. 31, 1988—Technology and Engineering—388 pages, pp. 2 and 4 Only.

International Searching Authority of the US Patent and Trademark Office, "International Search Report and Written Opinion" issued in related foreign patent application No. PCT/US14/65289, dated Jan. 21, 2015, 5 pages.

U.S. Food and Drug Administration, "Science and Our Food Supply. Examining Dietary Supplements. Teacher's Guide for High School Classroom", 1st Edition, from www.fda.gov/media/152680/download, 2021, 89 pages.

Units for vertical axis are Visual Analogue Scale (in cm).

Units for vertical axis are Visual Analogue Scale (in cm).

Units for vertical axis are Visual Analogue Scale (in cm).

Effect Size of 200 mg dose of TC over course of 7- day repeated dose study relative to baseline on: Fatigue: 0.64, Anxiety: -0.59, Libido: 0.71

Units for vertical axis are Visual Analogue Scale (in cm).

Effect Size of 200 mg dose of TC over course of 7- day repeated dose study relative to baseline on: Energy: 0.63, Motivation to Exercise: 0.58, Concentration: 0.60

Abbreviations: $MRT_{0-\infty}$, mean residence time zero to infinity; CL/F, oral clearance; Vz/F, oral volume of distribution; $AUC_{0-\infty}$, area under the curve from zero to time infinity (dose normalized); $C_{max}$, maximum plasma concentration (dose normalized); $T_{max}$, time to reach maximum plasma concentration.

Abbreviations: MRT$_{0-\infty}$, mean residence time zero to infinity; CL/F, oral clearance; Vz/F, oral volume of distribution; AUC$_{0-\infty}$, area under the curve from zero to time infinity (dose normalized); C$_{max}$, maximum plasma concentration (dose normalized); T$_{max}$, time to reach maximum plasma concentration.

Data are presented as mean ± standard deviation.

Data are presented as mean ± standard deviation.

Data are presented as mean ± standard deviation.

Data are presented as mean ± standard deviation.

ENHANCED CAFFEINATED BEVERAGE COMPOSITION

CROSS-REFERENCE TO RELATED APPLICATIONS

This application is a continuation of application Ser. No. 17/084,777 filed on Oct. 30, 2020, now U.S. Pat. No. 11,583,534, which is a continuation-in-part of application Ser. No. 16/551,373 filed on Aug. 26, 2019, now U.S. Pat. No. 11,426,410, which is a continuation of application Ser. No. 15/600,371, filed on May 19, 2017, now U.S. Pat. No. 10,398,701, which is a continuation-in-part of application Ser. No. 14/539,726, filed on Nov. 12, 2014, now U.S. Pat. No. 10,272,091, which claims the benefit of Provisional Application No. 61/903,362, filed on Nov. 12, 2013. This application also claims the benefit of U.S. Provisional Application No. 62/955,261, filed on Dec. 30, 2019. Each of the above applications is incorporated by reference in its entirety.

FIELD OF THE INVENTION

The field of the invention is a caffeinated beverage supplemented with theacrine and methylliberine.

BACKGROUND

The following description includes information that may be useful in understanding the present invention. It is not an admission that any of the information provided herein is prior art or relevant to the presently claimed invention, or that any publication specifically or implicitly referenced is prior art.

Tea and coffee are the most widely consumed products in the world. Tea and the different varieties of tea have been extensively studied. Many epidemiologic and preclinical studies suggest that drinking tea may reduce the risk of cancer and cardiovascular disease. Theacrine, an alkaloid purine similar to caffeine, is relatively rare and only found in a few varieties of tea (kucha tea, genus Camellia), the fruit cupuacu, and other plants related to coffee and cacao (genera Coffea and Theobroma), such as Coffea liberica, Coffea dewevrei, Coffea abeokutae and Theobroma grandiflorum.

1,3,7,9 tetramethyluric acid, commonly known as theacrine, was not studied until around 1975. However, it has been known of since about 1937, when it was detected in dry, decaffeinated Camellia sinensis tea leaves. At this time, the Camellia assamica var. kucha variety of tea is the primary source of naturally occurring theacrine and produces the chemical in higher concentrations than other known plants. Interestingly, theacrine has not been detected at all in more traditional teas strains. It is believed to be formed by methylation of caffeine and may be an intermediary in the production of liberine or other purines. Its natural function, if any, remains unknown. Theacrine has garnered attention only relatively recently, and often only as a secondary consideration when analyzing other compounds. Some studies suggest it may have beneficial qualities, such as serving as an effective anti-oxidant, anti-inflammatory and may have anti-obesity properties.

In the studies involving theacrine, beneficial effects may be at least partially attributable to an assortment of purine alkaloids and phenolic compounds. The more common tea-related purine alkaloids include caffeine, theobromine, theophyline and theacrine. The major tea phenolic compounds are gallic acid and eight naturally occurring tea catechins, including (+)– catechin (C), (−)-epicatechin (EC), (+)-gallocatechin (GC), (−)-epigallocatechin (EGC), (−)-catechin gallate (CG), (−)-gallocatechin gallate (GCG), (−)-epicatechin gallate (ECG) and (−)-epigallocatechin gallate (EGCG).

Many different biologic and physiologic activities have been attributed to tea and its various components. However, only a few of its components have been studied in depth. Caffeine is by far the most studied, and the most commonly used stimulant found in tea. Theacrine appears to have an opposite effect, despite being very similar in chemical structure. Recent experiments have shown that theacrine exhibits a variety of activities, some of which seem inconsistent.

In the past several years, there has been a substantial shift in public opinion toward using naturally occurring chemical compounds for a variety of purposes, instead of synthetic chemicals. For example, a wide variety of natural chemicals are now commonly used as sedatives, e.g. valerian root and chamomile, anti-depressants, e.g. St. John's wort, stimulants, e.g. caffeine, and concentration, e.g. ginseng. In general, naturally occurring compounds may be easier for the body to digest and interact with and may include minimal and less severe side effects.

It is therefore desirable to identify naturally occurring chemical compounds and mixtures thereof that may provide benefits. It is also desirable to provide chemical compounds and mixtures thereof that may be used to provide a variety of benefits, varying by concentration, thus requiring production or harvesting of fewer materials.

SUMMARY OF THE INVENTION

The inventive subject includes an enhanced caffeinated beverage supplemented with an effective blend of theacrine and methylliberine. The enhanced caffeinated beverage is a stimulating drink conferring an increase in mood, energy, alertness, focus, and/or motivation for the consumer (person consuming the enhanced caffeinated beverage), while not adversely increasing the person's heart rate or blood pressure.

Notably, in some embodiments, a caffeinated beverage composition is supplemented with methylliberine and theacrine. Most advantageously, the methylliberine and theacrine are in an effective synergistic combination imparting the desired mood, energy, alertness, focus, and/or motivation at increased levels relative to a caffeinated beverage alone as well as those experienced from a weight amount of methylliberine (e.g., 100 mg) that is greater than the total weight amount of effective blend of methylliberine and theacrine (e.g., 75 mg).

Embodiments of the contemplated subject matter include a caffeinated beverage composition supplemented with methylliberine and theacrine, wherein the caffeinated beverage composition includes a caffeinated drink having a caffeine content of between about 1 mg/oz to 65 mg/oz, theacrine in an amount of between about 1.5 mg/oz to 15 mg/oz, and methylliberine in an amount of between about 3.0 mg/oz to 30 mg/oz. In other embodiments, the caffeinated beverage composition includes a caffeinated drink having a caffeine content of between about 1 mg/oz to 65 mg/oz, theacrine in an amount of between about 1.5 mg/oz to 10 mg/oz, and methylliberine in an amount of between about 3.0 mg/oz to 20 mg/oz. In still other embodiments, the caffeinated beverage composition includes a caffeinated drink having a caffeine content of between about 1 mg/oz to 65 mg/oz, theacrine in an amount of between about 1.5 mg/oz to 5 mg/oz, and methylliberine in an amount of between about 3.0 mg/oz to 10 mg/oz. In preferred embodiments, theacrine and methylliberine are present in a weight ratio of between about 1:1.5 to 1:2.75 or 1:1.5 to 1:3.0. In exemplary embodiments, the theacrine and methylliberine are present in a weight ratio of between about 1:1.5 to 1:2.75.

In additional embodiments, the caffeinated drink is brewed coffee, tea, a cola, or an energy drink. In preferred embodiments, the caffeinated drink is brewed coffee. More preferably, the brewed coffee is a non-espresso coffee having a caffeine content of between about 10 to 30 mg/oz, or the brewed coffee is an espresso coffee having a caffeine content of between about 30 to 65 mg/oz in a volume of not more than 3 ounces.

In notable embodiments, the caffeinated beverage upon consumption by a person, increases mood, energy, alertness, motivation, and/or focus in the person compared to the caffeinated beverage alone or the caffeinated beverage supplemented only with methylliberine of between about 6 mg/oz or 12.5 mg/oz. In further embodiments, the caffeinated beverage does not adversely affect heart rate and/or blood pressure in the person. Additionally, the increased mood, energy, alertness, motivation, and/or focus in the person is experienced by the person up to about 5 hours after consumption of the caffeinated beverage composition.

In more specific embodiments, an enhanced coffee beverage includes a coffee drink supplemented with methylliberine and theacrine, wherein the coffee drink has a caffeine content of between about 1 mg/oz to 65 mg/oz, and the theacrine is in an amount of between about 1.5 mg/oz to 15 mg/oz, 1.5 mg/oz to 10 mg/oz, or 1.5 mg/oz to 5.0 mg/oz, and the methylliberine is added in an amount of between about 3.0 mg/oz to 30 mg/oz, 3.0 mg/oz to 20.0 mg/oz, or 3 mg/oz to 15 mg/oz, and wherein the theacrine and the methylliberine are in a weight ratio of between about 1:1.5 to 1:2.75 or 1:1.5 to 1:3.0.

Additional embodiments include a method of preparing an enhanced caffeinated beverage, including adding theacrine and methylliberine to a caffeinated drink, wherein the theacrine is added in an amount of between about 1.5 mg/oz to 15 mg/oz, 1.5 mg/oz to 10 mg/oz, or 1.5 mg/oz to 5.0 mg/oz, and the methylliberine is added in an amount of between about 3.0 mg/oz to 30 mg/oz, 3.0 mg/oz to 20.0 mg/oz, or 3 mg/oz to 15 mg/oz. In further embodiments, the method of preparing an enhanced caffeinated beverage includes a caffeinated drink selected from a brewed coffee, a tea, an energy drink, or a cola.

In preferred embodiments, the method of preparing an enhanced caffeinated beverage includes a brewed coffee wherein the adding of the theacrine and methylliberine are added to coffee grounds prior to brewing the brewed coffee or the theacrine and methylliberine are added to the brewed coffee. For example, the brewed coffee includes non-espresso or espresso brewed coffees, and/or the brewed coffee may be hot brewed or cold brewed.

Various objects, features, aspects and advantages of the inventive subject matter will become more apparent from the following detailed description of preferred embodiments, along with the accompanying drawing figures in which like numerals represent like components.

DETAILED DESCRIPTION

Figure 1:
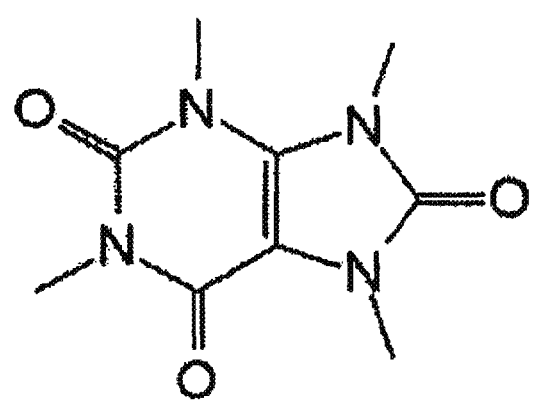
FIG. 1 depicts, in one embodiment, a molecular diagram of theacrine in accordance with the principles of the invention.

Before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

Disclosed is an invention relating to uses of theacrine, also known as 1,3,7,9-tetramethyluric acid, Temurin, Temorine, Tetramethyluric acid, Tetramethyl uric acid and 1,3,7,9-tetramethylpurine-2,6,8-trione. Theacrine may be produced synthetically or may be isolated from a natural source. Theacrine isolated from a natural source may be purified to 95% or greater. Optionally, less purification may be used such that theacrine accounts for 50%, or even less, of the material. In some embodiments, it may be preferable to utilize theacrine isolated from a natural source which may include other congeners of theacrine typically found in theacrine isolates.

Advantageously, the addition of an effective blend of theacrine (e.g., TeaCrine) together with methylliberine (MLL) (e.g., Dynamine) supplemented in a caffeinated beverage (e.g., brewed caffeinated coffee), results in an enhanced caffeinated beverage providing increased mood (e.g., positive mood), energy, motivation, alertness, focus, and/or decreased fatigue relative to a caffeinated drink supplemented with methylliberine alone at even greater amounts (e.g., 100 mg MLL) than the effective blend of methylliberine and theacrine (e.g., at a total of 75 mg). Furthermore, methylliberine and theacrine in a caffeinated beverage confers improved and desirable effects while tempering physiological side effects common to these stimulants. Most surprisingly, an effective blend of methylliberine and theacrine in caffeinated did not adversely affect blood pressure or heart rate.

As used herein, a caffeinated beverage is any consumable drink having caffeine. Examples of caffeinated drinks include coffee, tea (e.g., black or green), a cola drink (e.g., Coca-Cola®, Pepsi®, etc.), or an energy drink (e.g., Red Bull®, Monster®, or Wired®). For example, the energy drink is a non-coffee energy drink and/or a non-cola energy drink.

As used herein, a coffee drink refers to any type of coffee brewed from water and coffee grounds. The coffee drink may be hot brewed or cold brewed. The coffee drink may be a non-espresso coffee or an espresso brewed coffee. The coffee drink may be brewed using any suitable method. Examples of hot or cold coffee brewing methods include drip brew, French press, espresso brewing, modular non-espresso brewing using pods (e.g., Keurig®), or modular espresso brewing (e.g., Nespresso®). As well known in the art, brewing methods vary by size of coffee grounds, the water temperature passing over the grounds, and/or the pressure of the water passing over the grounds.

Notably, the contemplated caffeinated beverage supplemented with an effective blend of theacrine and methylliberine is a stimulating drink without negative physiological effects (e.g., increased heart rate or blood pressure) made of a synergistic combination of theacrine and methylliberine added to the caffeinated drink. In particular, the synergistic combination is an effective blend in which the theacrine and methylliberine are present in a weight ratio of between about 1:1.5 to 1:3.0 resulting in the supplemented caffeinated beverage having the advantageous and desired effects.

In more specific embodiments, the effective blend of theacrine and methylliberine in the enhanced caffeinated beverage is in a weight ratio of between about 1:1.5 to 1:2.75 or 1:1.5 to 1:3.0, and includes theacrine in an amount in milligrams per ounce (mg/oz) between about 1.5 mg/oz to 15 mg/oz, (0.05 mg/ml to 0.51 mg/ml) and methylliberine in an amount of between about 3.0 mg/oz to 30 mg/oz (0.10 mg/ml to 1.02 mg/ml). Accordingly, the disclosed effective blend of theacrine and methylliberine includes theacrine at an amount of between about 1.5, 1.6, 1.7, 1.8, 1.9. 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, or 15.0 gm/oz. Typically, the effective blend of theacrine and methylliberine includes theacrine at an amount of between about 2 mg/oz to 15 mg/oz, 2 mg/oz to 12 mg/oz, 2 mg/oz to 10 mg/oz, 2 mg/oz to 7 mg/oz, or 2 mg/oz to 5 mg/oz. More typically, the caffeinated drink is supplemented with theacrine at an amount of between about 2.5 mg/oz to 4.0 mg/oz. Most typically, the caffeinated drink is supplemented with theacrine at an amount of between about 2.75 mg/oz to 3.5 mg/oz. With respect to methylliberine, the disclosed effective blend of theacrine and methylliberine includes methylliberine in an amount of between about 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, or 15.0 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, or 30.0 mg/oz. Typically, the effective blend of theacrine and methylliberine includes methylliberine at an amount of between about 3 mg/oz to 25 mg/oz, 3 mg/oz to 20 mg/oz, 3 mg/oz to 19 mg/oz, 3 mg/oz to 18 mg/oz, 3 mg/oz to 17 mg/oz, 3 mg/oz to 16 mg/oz, 3 mg/oz to 15 mg/oz, 3 mg/oz to 14 mg/oz, 3 mg/oz to 13 mg/oz, 3 mg/oz to 12 mg/oz, 3 mg/oz to 11 mg/oz, 3 mg/oz to 10 mg/oz, 3 mg/oz to 9 mg/oz, or 3 mg/oz to 8 mg/oz. More typically, the caffeinated drink is supplemented with methylliberine at an amount of between about 5 mg/oz to 20 mg/oz, 5 mg/oz to 15 mg/oz, 5 mg/oz to 10 mg/oz. Most typically, the caffeinated drink is supplemented with methylliberine at an amount of between about 6.0 mg/oz to 8.0 mg/oz. For example, the caffeinated drink may be supplemented with methylliberine at an amount of between about 6.0 mg/oz to 7 mg/oz.

In other preferred embodiments, the enhanced caffeinated drink (e.g., coffee, tea, cola, or an energy drink) has a caffeine content in milligrams per ounce (mg/oz) of between about 1 mg/oz to 65 mg/oz (0.03 mg/ml to 2.2 mg/ml). For example, the caffeinated drink has a caffeine content of between about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, or 65 mg/oz. Typically, the caffeinated drink has a caffeine content of between about 10 mg/oz to 65 mg/oz, 15 mg/oz to 65 mg/oz, 20 mg/oz to 65 mg/oz. More typically, the caffeinated drink has a caffeine content of between about 10 mg/oz to 25 mg/oz.

In some embodiments, an enhanced caffeinated beverage is a coffee drink supplemented with the disclosed effective blend of theacrine and methylliberine. As disclosed herein, the coffee drink may be hot or cold brewed and may be a non-espresso brewed coffee or an espresso brewed coffee having a caffeine content of between about 1 mg/oz to 65 mg/oz. For espresso brewed coffee, the caffeine content is more typically about 40 to 65 mg/oz for a volume of not more than 3 ounces. For example, for an espresso coffee drink, the caffeine content is about 40 to 65 mg/oz with a total weight amount of both theacrine and methylliberine of about 15 to 30 mg/oz, e.g., 15-20 mg/oz for a 3.0 oz espresso or about 20-30 mg/oz for a 2 oz espresso. An espresso drink is typically not more than 3 oz and may also be 2 oz. For a non-espresso brewed coffee, the caffeine content is more typically about 10 to 30 mg/oz, 10 to 25 mg/oz, 10 to 20 mg/oz, or 15 to 25 mg/oz. Preferably, the coffee drink is supplemented with the disclosed effective blend of theacrine in an amount of between about 1.5 mg/oz to 15 mg/oz and methylliberine in an amount of between about 3.0 mg/oz to 30 mg/oz. More preferably, the coffee drink is supplemented with the disclosed effective blend of theacrine in an amount of between about 1.5 mg/oz to 15 mg/oz, 1.5 mg/oz to 10 mg/oz, or 1.5 mg/oz to 5.0 mg/oz, and the methylliberine is added in an amount of between about 3.0 mg/oz to 30 mg/oz, 3.0 mg/oz to 20.0 mg/oz, or 3 mg/oz to 15 mg/oz. In an exemplary embodiment, the coffee drink is supplemented with the disclosed effective blend of theacrine in an amount of between about 1.5 mg/oz to 15 mg/oz and methylliberine in an amount of between about 3.0 mg/oz to 30 mg/oz, wherein the theacrine and methylliberine are present in a weight ratio of between about 1:1.5 to 1:2.75.

As understood by skilled person, the effective blend disclosed herein of theacrine and methylliberine refers to the ratio of theacrine and methylliberine; however, the addition of theacrine and methylliberine to the brewed coffee may be carried out sequentially. That is, the effect of the combination of theacrine and methylliberine does not require that the theacrine and methylliberine ingredients are mixed prior to addition to the brewed coffee. Accordingly, methods for preparing the enhanced coffee beverage include supplementing the brewed coffee or coffee grounds with theacrine and methylliberine using any suitable method. In some embodiments, theacrine and methylliberine are added either sequentially or concurrently to brewed coffee. The theacrine and methylliberine may be added to a single serving of brewed coffee or may be added to a large stock of brewed coffee that is then served or packaged into smaller volumes. In other embodiments, one or both of the theacrine and methylliberine are added to the coffee grounds prior to the brewing process.

With reference to FIGS. 13A to 13H, results of a trial of volunteers consuming the enhance coffee beverage with 50 mg methylliberine and 25 mg theacrine showed increased mood (FIG. 13A), energy (FIG. 13B), motivation (FIG. 13C), alertness (FIG. 13D), decreased fatigue (FIG. 13E), and increased focus (FIG. 13F) as measured using a visual analogue scale (VAS) assessment as disclosed herein, compared to the reported effects after consumption of a decaffeinated coffee beverage, caffeinated coffee, coffee with 50 mg methylliberine, or coffee with 100 mg methylliberine. Accordingly, as shown in FIGS. 13A-13F, a caffeinated beverage (e.g., coffee) supplemented with the effective blend of theacrine and methylliberine, upon consumption by a person, increases mood, energy, alertness, motivation, and/or focus in the person compared to the caffeinated beverage alone or the caffeinated beverage supplemented only with methylliberine at 50 mg alone or 100 mg alone, or about 6 mg/oz or 12.5 mg/oz, respectively.

The increase in mood refers to an increase in a positive mood in which the person experiences increased content. The effects on mood, energy, alertness, focus, motivation, and/or decreased fatigue are observed at least as soon as 60 minutes after consumption of the enhance coffee beverage and may be experienced up to 5 hours (i.e., 300 minutes) after consumption. Not all effects may be experienced at the same time for the same duration. In typical embodiments, the effects on increased mood, energy, alertness, focus, motivation, and/or decreased fatigue are experienced at least as soon as 60 minutes from consumption up to 90 minutes, 2 hours, 2.5 hours, 3 hours, 3.5 hours, 4 hours, 4.5 hours, or 5 hours after consumption. In more typical embodiments, the effects on increased mood, energy, alertness, focus, motivation, and/or decreased fatigue are experienced at least as soon as 60 minutes from consumption up to 4 hours. In most typical embodiments, the effects on increased mood, energy, alertness, focus, motivation, and/or decreased fatigue are experienced at least as soon as 60 minutes from consumption up to 3 hours (180 minutes).

Furthermore, with reference to FIGS. 14A-14F, blood pressure (systolic and diabolic), heart rate, rate pressure product, mean arterial pressure, and pulse pressure showed no adverse effects, and in some cases were tempered relative to coffee supplemented with methylliberine alone. Accordingly, a caffeinated beverage (e.g., coffee) supplemented with the effective blend of theacrine and methylliberine, upon consumption by a person, increases mood, energy, alertness, motivation, and/or focus without adversely affecting blood pressure (systolic and diabolic), heart rate, rate pressure product, mean arterial pressure, and pulse pressure in the person.

In one embodiment, theacrine may be combined with other chemical compounds to provide a plurality of positive effects on a human or other animal. By altering the dosage of theacrine and/or chemical compounds it is combined with, various physiological effects may be selected for. The compositions may provide primarily a single benefit, or may provide multiple benefits simultaneously.

In another embodiment, theacrine may be used at lower dosage levels and/or in conjunction with compounds that modulate or antagonize its activity. Such compositions may induce an improved mood, higher energy, a reduction in fatigue, increased focus, increased concentration, increased mobility, decreased appetite, and increased stamina.

An advantage of using the invention may be the reduced likelihood that a person develops a tolerance to chemical compositions in accordance with the principles of the invention. That is, a person may not become desensitized to the effects induced.

In another embodiment, theacrine may be used at higher dosage levels and/or with synergistic compounds. These compositions may increase a person's basal/resting metabolic rate, increase thermogenesis, decrease appetite, enhance cognitive performance, increase Alpha wave brain activity, and/or induce euphoria. Without being bound by theory, the inventors believe that at higher dosage levels, theacrine may be noradrenergic and dopaminergic, and may exhibit increased adenosine receptor inhibition.

In another embodiment of the invention, theacrine may be combined with ephedrine, caffeine, salicylic acid or the like. These may be used to either modulate the more sedative effects of theacrine or optionally to interact synergistically with the more stimulating effects of theacrine. For example, theacrine may be combined with caffeine in order to modulate the excessive stimulatory effects of caffeine, thereby stabilizing heart rate and other metabolic activity. That is, a combination of theacrine and caffeine may result in a composition that imparts the increased focus and energy induced by caffeine, but without the higher heart rate and blood pressure due to modulation of caffeine by theacrine. Thus the combination may result in heightened awareness and calmness without the jitters caffeine may cause.

Theacrine and caffeine administered in combination has unexpected effects. Indeed, it has been unexpectedly found that a combination of theacrine and caffeine administered to human subjects results in increased levels of focus, concentration and energy as measured by 100 mm VAS scales while also decreasing measures of anxiety, irritability or feelings of overstimulation. Such decrease in anxiety, irritability, jitters and/or feelings of overstimulation is reflected by patients on standardized 100 mm VAS at durations of 30 minutes, 60 minutes, 120 minutes and 180 minutes as compared with administration of caffeine alone. The combination also exhibits a prolonged duration of action in increased energy, focus and/or concentration as compared to either caffeine or theacrine alone.

Furthermore, theacrine also has unexpected effects on the development of tolerance and habituation of caffeine. In a fourteen day study of repetitive dosing of theacrine and caffeine, it was found that the subjects maintained heightened psychometric indices of energy, focus, concentration, motivation to exercise, motivation to accomplish and finished tasks, and improved mood at Day 14 as compared to caffeine alone, and absolute levels of energy and motivation were greater than with theacrine alone. Those taking theacrine alone still maintained elevated subjective energy, focus, concentration, motivation to exercise, motivation to accomplish and finish tasks, sexual desire and improved mood with decreased anxiety as compared to Day 1. Subjects taking caffeine alone saw decreasing levels of energy, focus and concentration by Day 5 of the study and had increased anxiety scores throughout the study.

In another embodiment of the invention, theacrine may be combined with one or more bioavailability enhancers, including for example bioperine, piperine, black pepper, bergamottin, dihydroxybergamottin (CYP3A4 inhibitors), flavonoids (including hesperidin, naringin, tangeritin, quercetin and nobiletin both in isolation and in combination), pterostilbenes, fisetin, nanoencapsulation, microencapsulation, liposomes and/or phytosomes. Which enhancers are combined with theacrine may depend on which qualities of theacrine are desired for a particular use.

In another embodiment of the invention, theacrine may be introduced using one or more delivery methods, including, for example transdermal patches and/or creams, ready to mix powders, intravenous methods, capsules, tablets, liquid (including liquids for mixing with other beverages), softgels, shot format, and/or cosmetic applications including soaps, lotions and shampoos. Theacrine's anti-inflammatory qualities may be desired for a variety of topical applications.

In another embodiment of the invention, theacrine may be used to provide sports performance enhancers that may reduce fatigue, improve mobility, and improve alertness.

In another embodiment of the invention, theacrine may be used as a topical agent for incorporation into body creams or lotions to produce a cream or lotion for lightening skin, firming skin, and/or improving skin elasticity. A theacrine topical agent may also be used to promote localized transdermal fat loss. Theacrine may also be used in a cream or lotion to promote localized enhanced metabolism and/or enhanced thermogenesis.

In another embodiment of the invention, theacrine may be combined with one or more of an analgesic, for example ibuprofen or salicylic acid, anti-inflammatory agents, salicin, fish oil (omega-3 fatty acids and specialized, small lipid pro-resolving derivatives), tart cherry, krill oil, astaxanthin, proteolytic enzymes, glucosamine sulfate, chondroitin sulfate, MSM (methyl sulfonylmethane), SAMe (S-adenosylmethionine), ASU (avocado-soybean unsapponifiable fraction), cetyl myristoleate, Dolichos falcate and/or triterpenoids.

Theacrine itself can reduce biomarkers of inflammation in humans in response to acute inflammatory stressors (e.g., intense exercise) or chronic consumption. Theacrine is shown to decrease C-reactive protein (CRP), Erythrocyte sedimentation rate (ESR), interleukin-6 (IL-6) and TNF-alpha.

In another embodiment of the invention, theacrine may be combined with extracts from one or more of Acacia catechu, Andrographis paniculata, Scutalleria baicalensis, agmatine sulfate, Stinging Nettle, Sea Buckthorn, curcumin, Cissus Quadrilangularis, Boswellia Serrata, Wasabia japonica (wasabi extract for Tea Tree Oil), Emu Oil, Arnica, Mangifera indica L. (Anacardiaceae), Lagenaria breviflora, and/or Zingiber officinale (ginger & gingerols/shogaols). Such a combination may be used in, for example, methods of augmenting and enhancing pain modulation, and controlling the inflammatory response.

In another embodiment of the invention, theacrine may be combined with one or more metabolic enhancers including Hoodia gordonii, caffeine, yohimbine, synephrine, theobromine, flavonoids, flavanone glycosides such as naringin and hesperidin, tocopherols, theophylline, alpha-yohimbine, conjugated linoleic acid (CLA), octopamine, evodiamine, passion flower, red pepper, cayenne, raspberry ketone, guggul, green tea, guarana, kola nut, any beta-phenethylamines, Acacia rigidula, and/or forskolin (Coleus forskohlli). Such a combination may be used in, for example, methods of enhancing 1) thermogenesis/fat and carbohydrate metabolism; 2) fat loss, weight management and improving body composition (loss of body fat, while retaining or sparing lean body mass/fat free mass/muscle); and/or 3) appetite control/appetite modulation.

Combinations of theacrine and, for example, caffeine, theobromine, or flavanone glycosides such as naringin or hesperidin, upon administration to subjects show decreased VAS 100 mm ratings of perceived physical exertion with exercise as compared to ingredients alone. Theobromine is used by some for improvement of breathing or a subjective feeling of improved breathing, but is also known to increase feelings of anxiety, jitters and an elevated heart rate in some subjects. A combination of theobromine and theacrine retains the beneficial effects while reducing the unwanted anxiety, jitters and/or elevated heart rate effects.

In another embodiment of the invention, theacrine may be combined with anti-fatigue, focusing and/or energy enhancing ingredients including caffeine, theobromine, theophylline, synephrine, yohimbine, rhodiola, ashwagandha, ginseng, Ginkgo biloba, siberian ginseng, astragalus, licorice, green tea, reishi, dehydroepiandrosterone (DHEA), pregnenolone, tyrosine, N-acetyl-tyrosine, glucuronolactone, taurine, choline, CDP-choline, alpha-GPC, acetyl-L-carnitine, 5-hydroxytryptophan, tryptophan, any beta-phenethylamines, Sceletium tortuosum (and Mesembrine alkaloids), Dendrobium sp., Acacia rigidula, PQQ (Pyroloquinoline quinone), Ubiquinone(ol), nicotinamide riboside, picamilon, Huperzine A (Chinese clubmoss) or Huperzia serrata, L-dopa, Mucuna pruriens, forskolin (Coleus forskohlli). Such a combination may be used in, for example, methods for enhancing cognitive function, including focus, concentration, sustained attention, working memory, choice and non-choice reaction time, executive function, verbal and non-verbal learning, visuospatial memory and verbal fluency.

In a further embodiment, theacrine may be combined with a nutritional cholinergic ingredient such as 2-(dimethylamino)ethanol (DMAE), DMAE bitartrate, choline bitartrate, alpha-GPC (alpha-glycerophosphorylcholine), Huperzine A, CDP choline, or combinations thereof. One of skill in the art will recognize that these are merely examples of cholinergic ingredients and that other such cholinergic ingredients not listed are also contemplated by the present invention. The combination of a nutritional cholinergic ingredient with theacrine can result in a synergistic effect of increased psychometric measures for attention, focus and concentration beyond either the theacrine alone or cholinergic ingredient alone.

In another embodiment, any of the above combinations may be used with an isomer of, congener of, derivative of and/or a metabolite of theacrine such as, for example, liberine or methylliberine. Other suitable examples include methylated theacrine, nitrate salts of theacrine, oxidized theacrine, reduced theacrine and/or theacrine salts. Agglomerated theacrine, microencapsulated theacrine, liposomal theacrine, esterified theacrine, theacrine glycerides, and mixtures of theacrine with propylene glycol, lauroyl Macrogol, polyethylene glycol, theacrine derivatives, and/or theacrine co-crystallization products may also be used in accordance with the principles of the invention. Such use of these, as well as co-crystals or other conjugates (such as quercetin or pterostilbenoids), theacrine salts including citrate, salicylate, malate, tartrate, fumarate, succinate, nitrate, sulfate, phosphate and the like, or PEG-ylated (Macrogol) preparations may increase the functional efficacy of the theacrine.

In another embodiment, congeners of theacrine, for example catechins and other flavonoids, may be used an isolated, either independently or in combination with theacrine-based compositions.

The dosage of theacrine may range from about 5 mg to about 850 mg. In another embodiment, the range may be from about 65 mg to about 300 mg. In relation to the weight of the human subject, in one embodiment the dosage may be expressed as about 0.75 mg/kg of body weight to about 3 mg/kg of body weight. In initial trials the human ED90 appears to be about 1 mg/kg to about 3 mg/kg.

In one aspect of the invention, the theacrine may be administered with caffeine. When administered with caffeine, the ratio of caffeine to theacrine, weight to weight, may range from about 0.5:1 to about 50:1, and in another embodiment, from about 1:1 to about 10:1, and in a further embodiment, from about 2:1 to about 4:1. In administration, the theacrine may be administered in an amount of about 5 mg to about 800 mg with caffeine amounts ranging from about 25 mg to about 650 mg. In another embodiment the theacrine may be administered in an amount of about 5 mg to about 650 mg with the caffeine, and in other embodiments may be any amount in that range. Such administration provides an increase, as measured by 100 mm VAS scales, in at least one of focus, concentration and energy, while also providing a decrease in at least one of anxiety, irritability, and feelings of overstimulation. Recommended dosages expressed in terms of amount per body weight can range from about 0.75 mg/kg to about 3 mg/kg of theacrine when administered in combination with caffeine, although theacrine may be administered in the ranges described above up to about 850 mg regardless of whether it is administered in combination with caffeine.

The invention may be used for the treatment of a variety of conditions, such as improvement of mood, energy, focus, or concentration. The invention may also promote a reduced appetite, reduce the perceived exertion from exercise, decrease the discomfort associated with intense exercise, and may also improve sexual desire.

The discussion herein provides many example embodiments of the inventive subject matter. Although each embodiment represents a single combination of inventive elements, the inventive subject matter is considered to include all possible combinations of the disclosed elements. Thus, if one embodiment comprises elements A, B, and C, and a second embodiment comprises elements B and D, then the inventive subject matter is also considered to include other remaining combinations of A, B, C, or D, even if not explicitly disclosed.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

Furthermore, the recitation of ranges of values herein is merely intended to serve as a shorthand method of referring individually to each separate value falling within the range. Unless otherwise indicated herein, each individual value with a range is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

EXAMPLES

Example 1

In order to examine the beneficial experiential effects and psychometric properties of theacrine supplementation in healthy subjects, explore optimal dosing and potential cumulative effects in a healthy human cohort with a 7-day, sub-acute repetitive dosing protocol, and acquire preliminary data on various biomarkers of safety and tolerability, an experiment was performed.

15 healthy subjects (mean ±SD age, height, wgt, BMI: 28.3 ±6.1 y, 175.7 +11.5 cm, 89.8 ±21.7 kg, 29.1 ±4.7) ingested 200 mg of TeaCrine™ (Compound Solutions, Inc., Carlsbad, Calif) (TC) or Placebo (PLA). Anchored VAS questionnaires were used to detect changes in various aspects of physical and mental energy and performance; side effect profiles, hemodynamics and biochemical markers of safety were also collected over a 3-hr post-dosing period. A subset of 6 subjects underwent a separate 7-day, open-label, repeated dose study comparing 100 mg, 200 mg and 400 mg of TC.

The experiment was a randomized, placebo-controlled, double-blind, within-subject crossover clinical trial (for N=15 study). A further subset study was open-label, sub-acute (7-day), repetitive dosing trial (for N=6 subset).

Six (6) subjects provided written and dated informed consent to participate in the 7-day repetitive dosing study between Dec. 15, 2012 and Feb. 21, 2013. A separate cohort of fifteen (15) subjects provided written and dated informed consent for the acute dose, placebo-controlled, crossover clinical trial. All subjects were in good health as determined by physical examination and medical history, between the ages of 18 and 45 (inclusive). Subjects' caffeine intake from foods/beverages was limited to <300 mg daily. Subjects were willing and able to comply with the experimental and supplement protocol.

Excluded subjects included subjects who were pregnant or lactating, subjects with a history of hepatorenal, musculoskeletal, autoimmune, or neurologic disease, diabetes, thyroid disease, adrenal disease, hypogonadism, inborn error of metabolism, personal history of heart disease, high blood pressure (systolic >140 mm Hg & diastolic >90 mm Hg), psychiatric disorders, cancer, benign prostate hypertrophy, caffeine sensitivity, gastric ulcer, reflux disease, or any other medical condition deemed exclusionary by the medical staff, subjects currently taking thyroid, hyperlipidemic, hypoglycemic, anti-hypertensive, anti-coagulant medications or OTC products containing pseudoephedrine or other stimulants, subjects who had used any weight-loss supplements within 30-days prior to the study, subjects who had gained or lost more than 10 lbs within the past 30 days, subjects who drank more than one cup of percolated coffee or 2 cups of tea per day, subjects who smoked or had quit smoking within the past six months, subjects who had a known allergy to any of the ingredients in the supplement or the placebo, and subjects who did not demonstrate a verbal understanding of the Informed Consent document.

Physical activity levels and health history were determined using standardized questionnaires. Heart rate and blood pressure were measured using an Omron HEM-780. Standing height was determined using a wall-mounted stadiometer. Body weight was measured using a Seca 767.™ Medical Scale. A 100 mm anchored VAS questionnaire for energy, fatigue, and concentration was distributed at each acute lab session; additional VAS questionnaires were distributed for the daily assessment over a 6-hour period during the 7-day subset study. Quest Diagnostics (Pittsburgh, Pa.) was utilized to transport and analyze all blood samples. For each laboratory session, subjects reported to the lab well hydrated, 10-12 hours postprandial, and at least 24-hours after their last exercise session.

Statistical Analyses for Example 1. Descriptive statistics (mean, median, SD, 95% CIs) were used to quantify subjects physical characteristics. RM ANOVA, as well analyses of co-variance (ANCOVA), using baseline scores as the co-variate (respectively), were used to analyze between trial differences. Alpha was set to 0.05 (P.ltoreq.0.05) for statistical significance, and <0.10 for trends. Effect sizes were also calculated. Upon arrival for the first testing session, subjects were randomly assigned to receive their respective supplement/placebo. Each subject ingested the sponsor recommended dosage of their respective supplement (1 capsule prior to schedule of assessments). Supplements were prepared in capsule form and packaged in coded generic containers for double-blind administration.

The 200 mg dose of TC caused significant improvements in energy (TC: +8.6% vs. PLA: −5.7%, P=0.049) and reductions in fatigue (TC: −6.7% vs. PLA: +5.8%, P=0.04). A trend for improved concentration was also noted (TC: +2.4% vs. PLA: −1.3%, P=0.07). No changes in systemic hemodynamics or side effect profiles were noted. The N=6 cohort study demonstrated moderate to large effect sizes (0.50 to 0.71) with the 200 mg dose of TC over a 7-day period of assessment for the following subjective measures: energy, fatigue, concentration, anxiety, motivation to exercise and libido.

The results of the experiment are also shown graphically in FIGS. 2 through 7.

Figure 2:
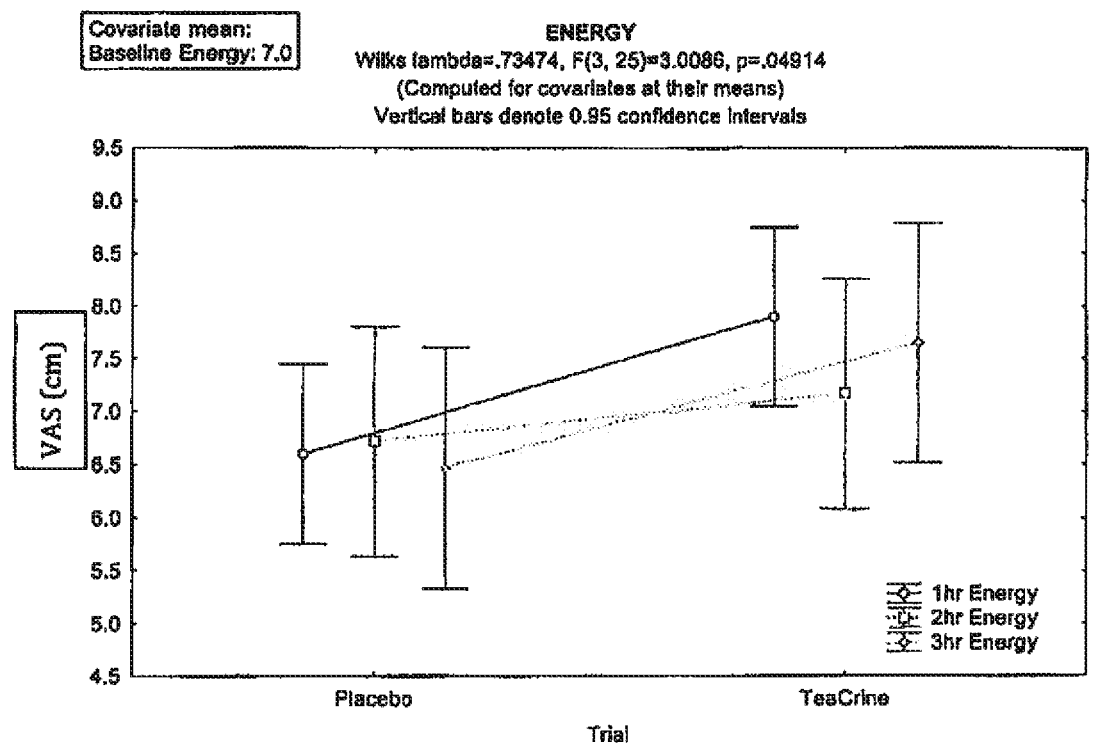
FIG. 2 depicts, in one embodiment, a graph of results of a trial showing perceived energy on a Visual Analogue Scale (VAS) scale (0 to 10 cm) at 1, 2 and 3 hours after administration of theacrine or placebo.
Figure 3:
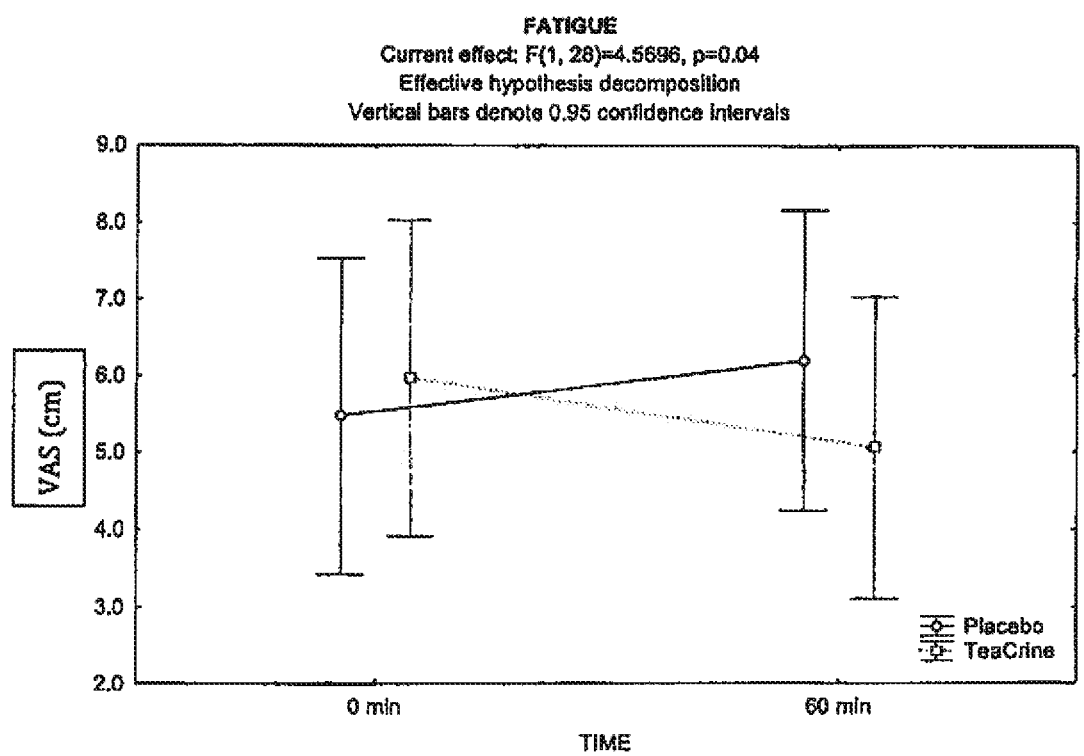
FIG. 3 depicts, in one embodiment, a graph of results of a trial showing perceived fatigue on a VAS scale (0 to 10 cm) at 0 minutes and 60 minutes after administration of theacrine or placebo.
Figure 4:
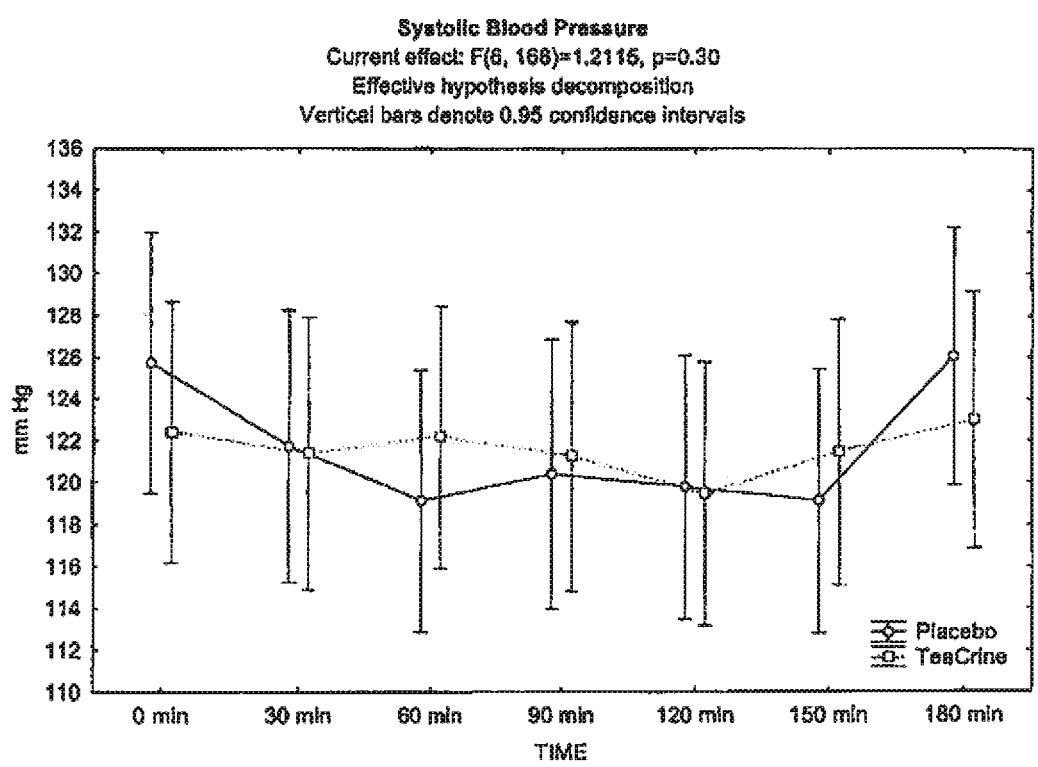
FIG. 4 depicts, in one embodiment, a graph of results of a trial showing systolic blood pressure at various time intervals after administration of theacrine or placebo.
Figure 5:
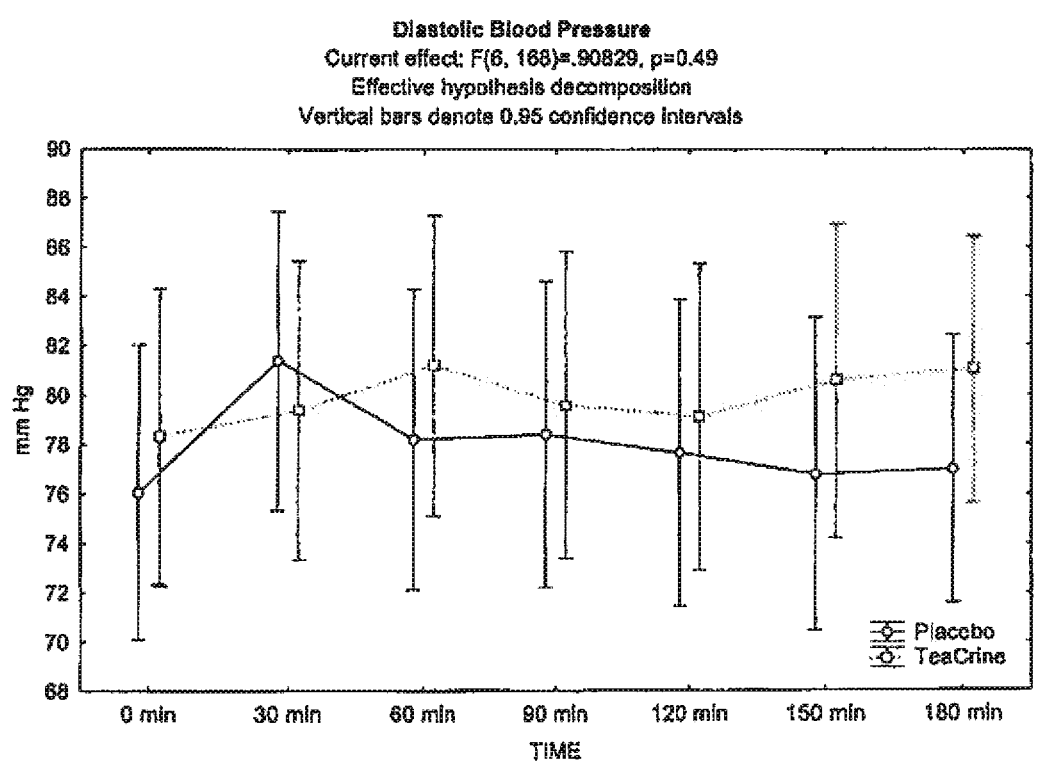
FIG. 5 depicts, in one embodiment, a graph of results of a trial showing diastolic blood pressure at various time intervals after administration of theacrine or placebo.

As shown in FIG. 2, individuals who were administered theacrine reported higher levels of energy at each time increment measured. FIG. 3 shows that while individuals given the placebo reported higher fatigue at 60 minutes after administration, those administered theacrine reported lower levels of fatigue. FIGS. 4 and 5 show that no substantial change in systemic hemodynamics occurred.

Figure 6:
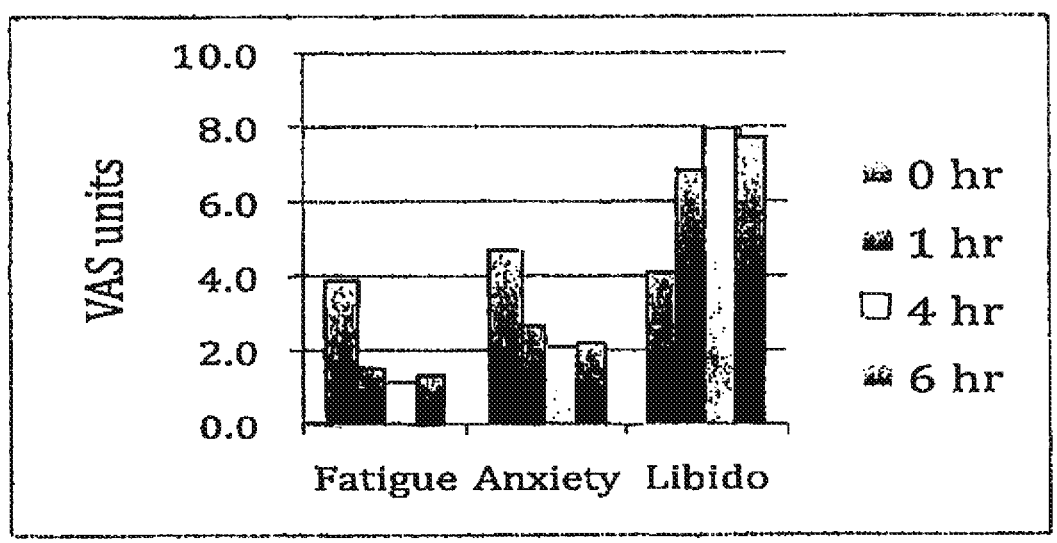
FIG. 6 shows, in one embodiment, the results of a 7 day repeated dose study of 200 mg theacrine relative to baseline of fatigue, anxiety and libido at various intervals after dosages (at 0 hr, 1 hr, 4 hr, 6 hr; bars left to right for each measured category).
Figure 7:
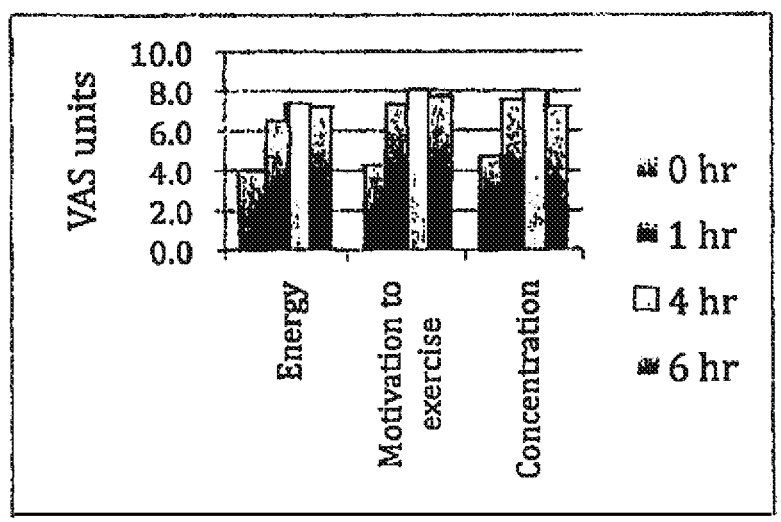
FIG. 7 shows, in one embodiment, the results of a 7 day repeated dose study of 200 mg theacrine relative to baseline of energy, motivation to exercise, and concentration at various intervals after dosages (at 0 hr, 1 hr, 4 hr, 6 hr; bars left to right for each measured category).

FIGS. 6 and 7 show the results of the N=6 cohort study. With a 200 mg dose of theacrine over a 7 day period of assessment, it was observed that theacrine has a positive effect on each of energy, fatigue, concentration, anxiety, motivation to exercise, and libido. That is, fatigue and anxiety were decreased substantially, while energy, concentration, motivation to exercise and libido were increased substantially.

Thus, the experimental data shows that theacrine supplementation appears to favorably impact several subjective and psychometric indices of energy and fatigue. These findings, as well as the potential cumulative effects on focus, concentration, and libido are worthy of future study.

Although previously published animal data suggested much larger doses of "TC" would be necessary to exert its neurophysiological effects, this first-in-human data suggests much lower doses of 1.5 mg to 2.5 mg/kg bodyweight (for example, approximately 200 mg in a 100 kg individual) provide optimal benefit. Follow-up studies should confirm these results, explore other objective measures of physical and cognitive function, and clarify the mechanisms by which theacrine exerts the observed salutary effects.

Assessment of the Drug-Drug Interaction Potential Between Theacrine and Caffeine in Humans Example 2

Theacrine pharmacokinetics in humans has not been systematically characterized. Therefore, one purpose of this study, among others, was to determine theacrine pharmacokinetics and dose-linearity following oral administration in humans. Another purpose of this study is to determine whether or not caffeine alters theacrine pharmacokinetics and/or pharmacodynamics, when both ingredients are ingested together.

Eight healthy nonsmokers, including 4 men and 4 women, were recruited for the experiment. The test subjects regularly consumed stimulants (i.e., caffeine, 50-400 mg/day) with beverages or nutritional supplements. The same test subjects did not have a history of adverse reactions to caffeine or other stimulants.

Study Design and Procedures. This study was a randomized, double-blind, 4-arm crossover design with each subject receiving 4 treatments consisting of theacrine (25 mg), theacrine (125 mg), caffeine (150 mg), and theacrine (125 mg) plus caffeine (150 mg), respectively. Theacrine, administered as iTeaCrine.®, was provided by Compound Solutions (Carlsbad, Calif). Caffeine, administered as caffeine anhydrous, was obtained from Nutravative Ingredients (Allen, Tex.). Treatment sequence was randomized using a 4.times.4 Latin square. There was an approximate 1-week washout period between treatments for all subjects.

Test Visit Procedures. Each study day, subjects reported to the lab between 6:00 and 7:00 am after a 10-hour fast and abstinence from beverages, drugs, or supplements containing alcohol or caffeine (72-hours) and strenuous physical exercise (24-hours). A catheter was inserted into the forearm vein for blood sampling. Duplicate measurements of resting heart rate and blood pressure were taken pre-dose and prior to each timed blood sample. In addition, respiratory rate was counted in one minute and body temperature was measured using an ear scanning thermometer (dual readings taken at each time). At approximately 8:00 am, each subject received a single oral dose of a theacrine, caffeine, or combined theacrine-caffeine composition accompanied by water. Blood samples at 0 minute (5 samples obtained for baseline prior to administration of the oral compositions), 15 minutes, 30 minutes, 60 minutes, and 90 minutes, and 2, 4, 6, 8, and 24 hours post-administration. Collected samples were processed and stored in multiple aliquots (.about.500 µL, −70.degree. C.) until analyzed for theacrine, caffeine, and paraxanthine using LC-MS/MS.

All subjects were instructed to consume their usual diet throughout the study period, with the exception of the actual days of testing. During the two days prior to each test day, subjects recorded all food and drink consumed and attempted to mimic this intake for the two-day period prior to subsequent visits. Diet records were analyzed using nutrient analysis software (Food Processor SQL, version 9.9; ESHA Research, Salem, Oreg.). For the actual test days, standardized meals (meal replacement food bars [Clif "Builder's 20 g Protein Bar"] and ready-to-drink shakes [Orgain Organic Nutrition™]) were provided to the subjects after sample collection at hour 2 and hour 6 (one shake and one-half bar at each time). Subjects were also provided with adequate meal replacement bars and shakes to consume following the 8 hour sample collection. (during their time outside the lab). Each bar contained 280 calories, 10 grams of fat, 29 grams of carbohydrate, and 20 grams of protein.

Each shake contained 250 calories, 7 grams of fat, 32 grams of carbohydrate, and 16 grams of protein. No food other than what was provided to the subjects was allowed during each study day, including both time spent in the lab and outside the lab. The only beverage that the subjects were allowed to consume was water and the volume consumed while in the lab was matched for each test day (men: 94 ±25 ounces; women: 78 ±17 ounces). The subjects returned the following morning for the 24 hour blood collection, again in a 10 hour fasted state. The same volume of meal replacement bars or shakes was consumed by each subject during each visit (both in lab and outside lab). All the subjects except one female consumed 3 shakes and 3 bars during the period of time outside the lab. Said female subject only consumed 2 bars and 2 shakes. Physical activity remained similar for all the subjects throughout the study period, with the exception of refraining from strenuous physical activity during the 24-hour period prior to each test day and for the actual test day itself.

Pharmacokinetic Study. Plasma concentration-time data were evaluated using noncompartmental methods in Phoenix WinNonlin (version 7.0; Pharsight Corporation, Mountain View, Calif) with adjustment for lag time after oral administration. The maximum concentration ($C_{max}$), lag time ($ta_{lag}$), and time of maximum concentration ($t_{max}$) were determined from the plasma concentration versus time data. The area under the plasma concentration-time curve from time 0 to infinity (was calculated using the trapezoidal rule extrapolated to time infinity). The terminal half-life ($t_{1/2}$) was calculated using the following function: $t_{1/2}=0.693/k$, wherein k is the constant of terminal rate elimination estimated from the slope of the linear portion of the log plasma concentration versus time curve. The oral clearance (CL/F) was calculated by dividing the oral dose by $AUC_{0-\infty}$. The apparent volume of distribution during the terminal elimination phase (Vz/F) was calculated by dividing CL/F by k.

Statistical Analysis for Example 2. Differences between treatment group values were determined for systolic blood pressure (SBP), diastolic blood pressure (DBP), rate pressure product, and heart rate. Parametric data were analyzed by paired Student's t tests of mean differences in values between treatment groups. Statistical significance was defined a priori as a 2-sided or <0.05. The probability of interaction magnitude between theacrine and caffeine was determined using 90% confidence intervals about the geometric mean ratio of the observed pharmacokinetic parameters.

Results. Subject characteristics. Eight physically active and healthy men (n=4; age 34.5 ±7.0 years; weight 94.3 +13.1 kg) and women (n=4; age 22.5 ±3.9 years; weight 66.4 ±10.1 kg) completed this study. Men ingested a daily amount of caffeine equal to 143.8 ±168.7 mg, while women ingested 144.3 +139.7 mg. All the subjects tolerated the treatments well and no adverse events were noted. Dietary intake was not different across treatment conditions for calories, macronutrients, or micronutrients (p>0.05).

Figure 8A:
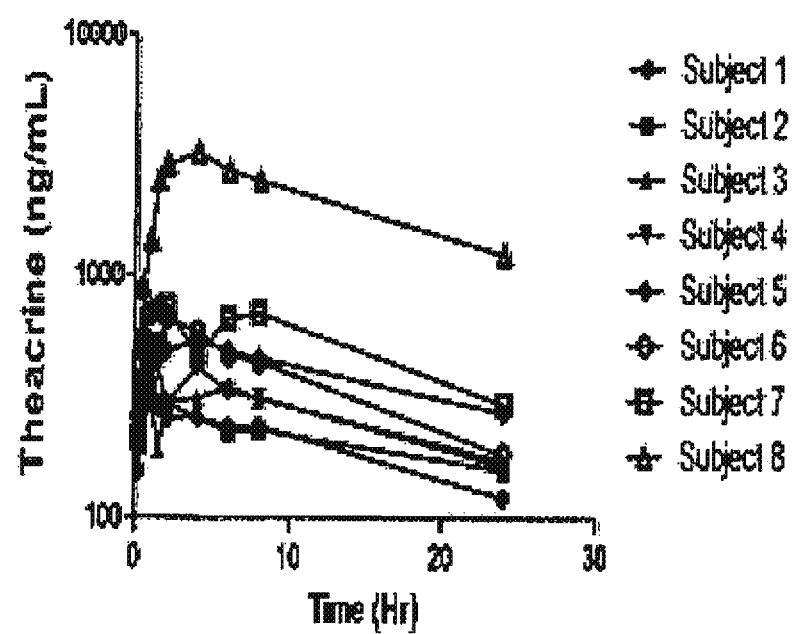
FIG. 8(A) depicts, in one embodiment, individual plasma concentrations of theacrine after single oral dose of theacrine 25 mg.
Figure 8B:
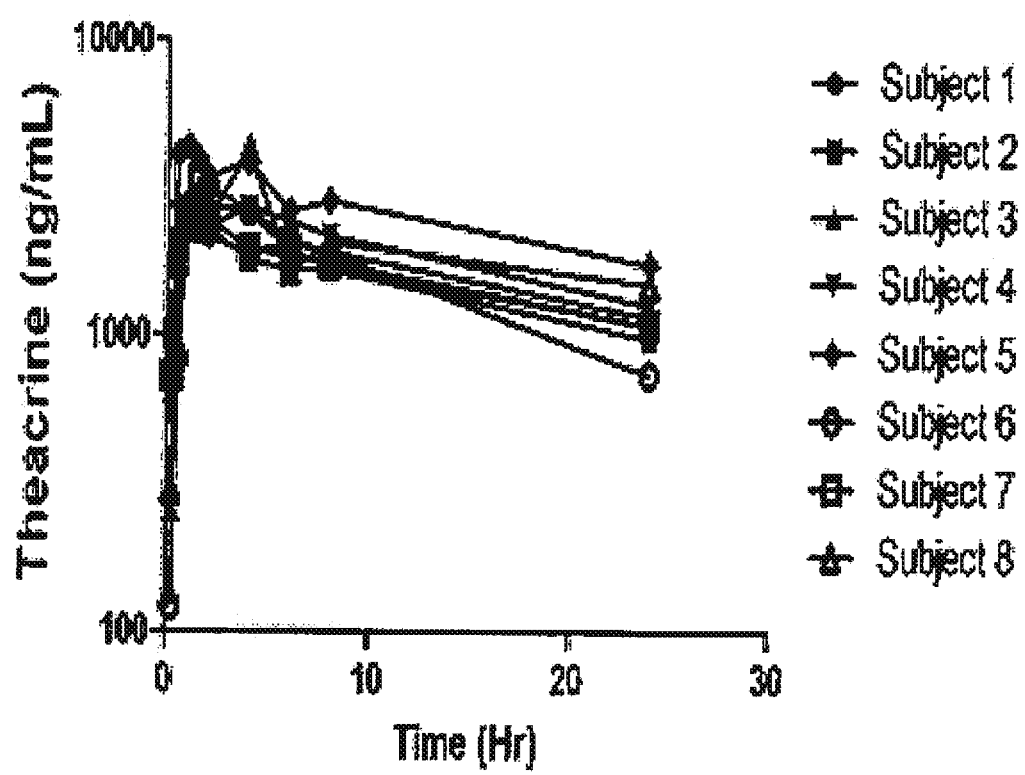
FIG. 8(B) depicts, in one embodiment, individual plasma concentrations of theacrine after single oral dose of theacrine 125 mg.
Figure 8C:
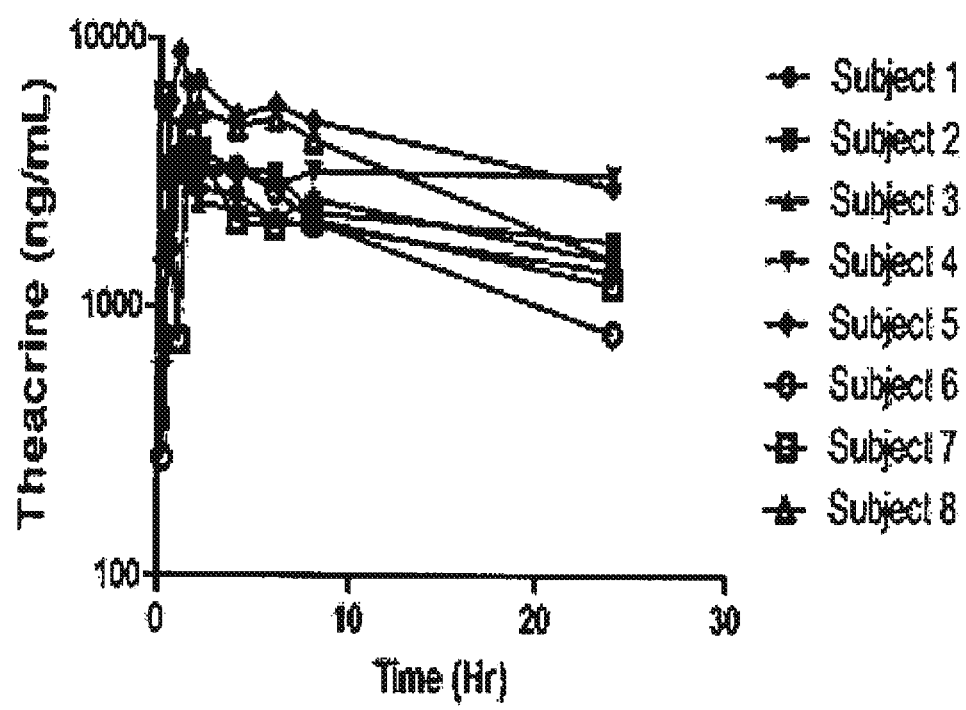
FIG. 8(C) depicts, in one embodiment, individual plasma concentrations of theacrine after single oral dose of theacrine 125 mg plus caffeine 150 mg.
Figure 9:
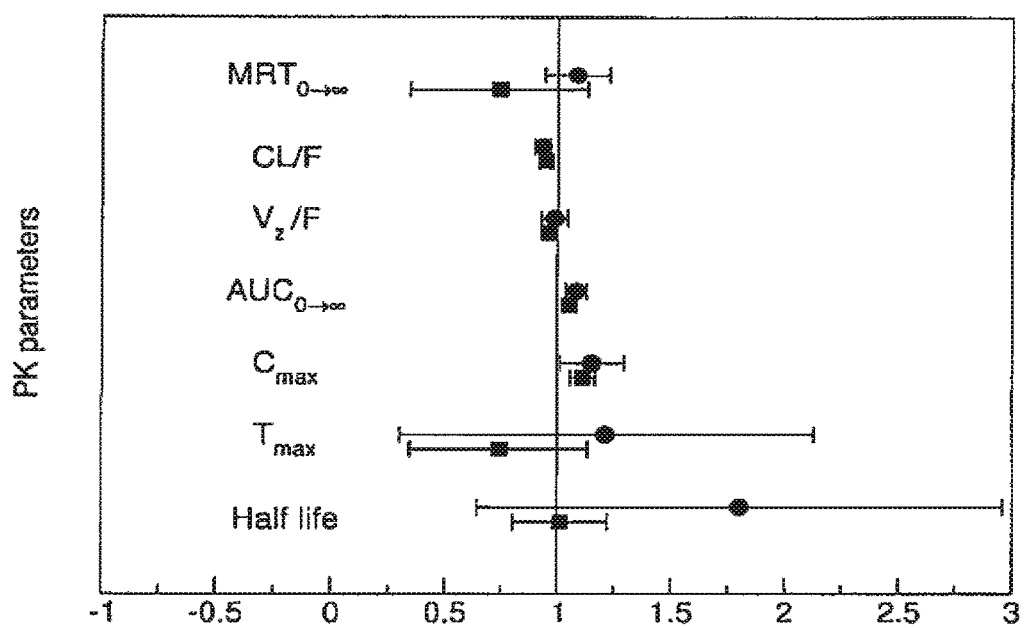
FIG. 9 depicts, in one embodiment, Forest plot illustrating the probability of interaction magnitude between theacrine and caffeine using 90% confidence intervals about the geometric mean ratio of the observed pharmacokinetic parameters following a single theacrine dose (-●- 25 mg theacrine and -■- 125 mg theacrine in combination with 150 mg caffeine).
Figure 10A:
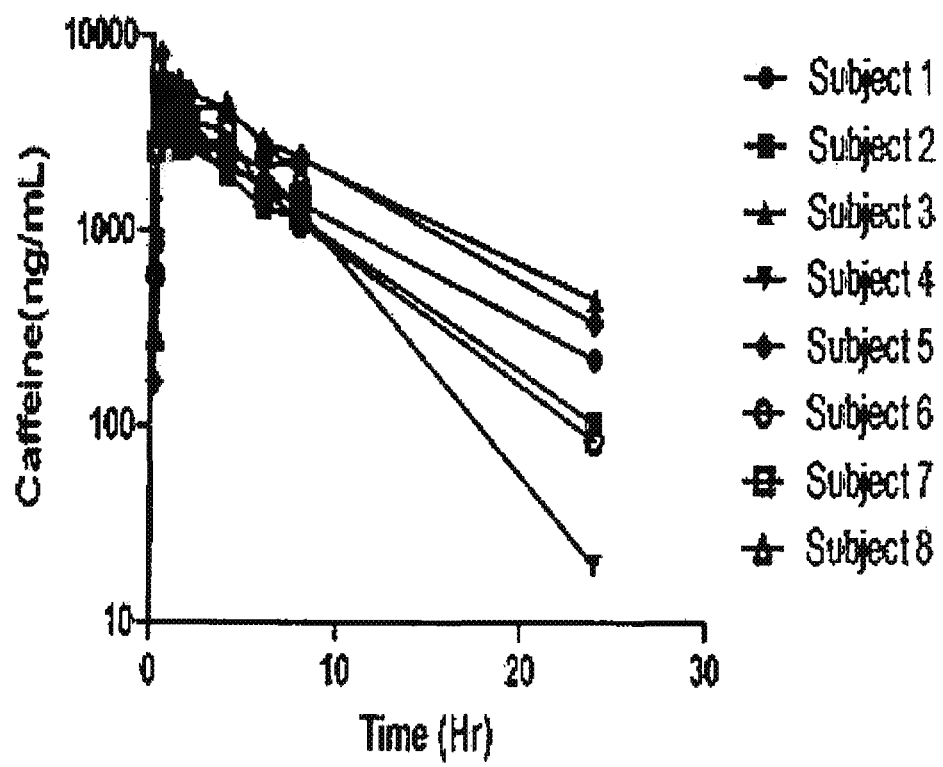
FIG. 10(A) depicts, in one embodiment, individual plasma concentrations of caffeine after single oral dose of caffeine 150 mg.
Figure 10B:
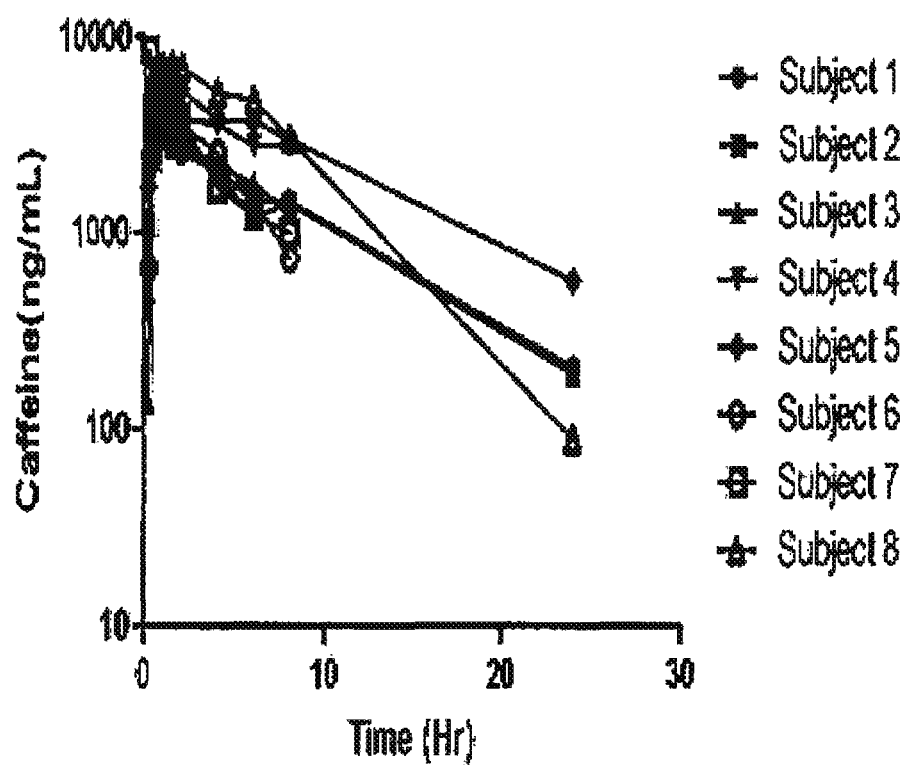
FIG. 10(B) depicts, in one embodiment, individual plasma concentrations of caffeine after single oral dose of theacrine 125 mg plus caffeine 150 mg.

Pharmacokinetics. Mean plasma concentration time profiles for theacrine, caffeine, and paraxanthine are shown in FIGS. 8, 9, and 10. Theacrine is well absorbed following oral administration of theacrine alone reaching maximal concentration within approximately 2 hours. Dose-adjusted theacrine pharmacokinetic parameters were not significantly different (Table 1). Theacrine absorption rate ($T_{max}$) and half-life ($t_{1/2}$) were unaffected by caffeine co-administration. However, caffeine co-administration significantly increased both mean theacrine exposure parameters $C_{max}$, (38.6 ±16.6 versus 25.6 ±5.5 ng/mL) and AUC (1.2 ±1.1 versus 0.74

Figure 11:
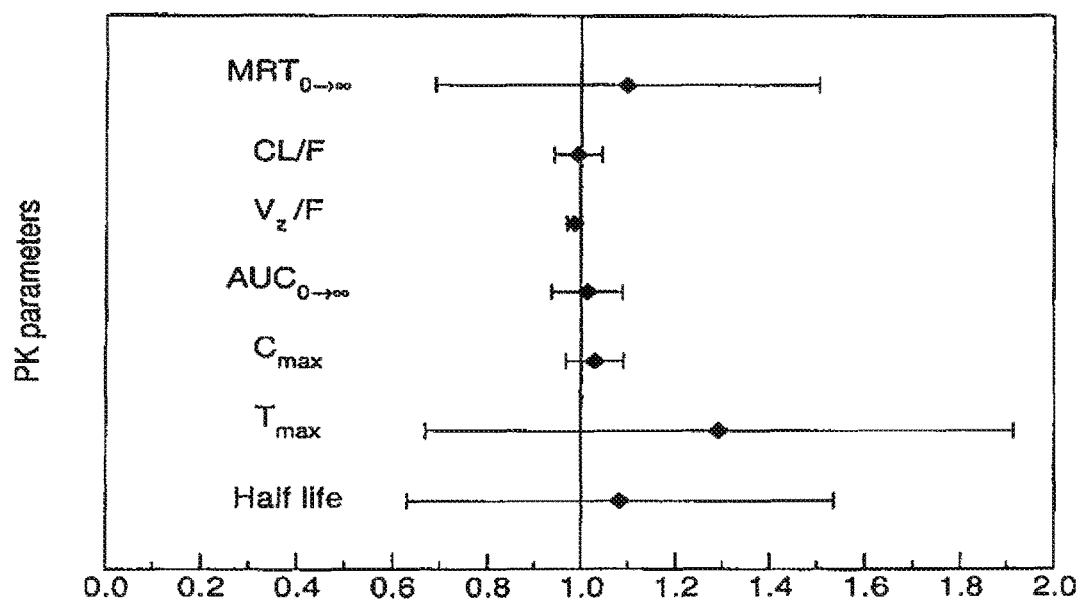
FIG. 11 depicts, in one embodiment, Forest plot illustrating the probability of interaction magnitude between caffeine and theacrine using 90% confidence intervals about the geometric mean ratio of the observed pharmacokinetic parameters following a single caffeine dose (150 mg) alone or in combination with theacrine (125 mg).

±0.31 hr*µg/mL/mg) as well as geometric mean ratios (1.1 ±0.06 and 1.1 ±0.03) (Table 2). Moreover, caffeine decreased both theacrine oral clearance (CL/F, 1.6 ±0.49 versus 1.2. ±0.56 L/hr) and oral volume of distribution (Vd/F, 50.5 ±0.49 versus 35.4 +12.4 L) by approximately 30%. Of note, theacrine exposure (AUC) was consistently higher in Subject 8 than all other subjects in all treatment arms. However, caffeine pharmacokinetics in Subject 8 was similar to the other seven subjects. Caffeine pharmacokinetics is similar following caffeine alone or caffeine plus theacrine co-ingestion (FIGS. 10 and 11 and Table 2). Likewise, theacrine co-ingestion did not alter paraxanthine exposure parameters suggesting caffeine metabolism was unaffected by theacrine (Table 3).

TABLE 1

Theacrine Pharmacokinetics

| Parameter[a] | Condition 1[b] | Condition 2[c] | Condition 4[d] |
|---|---|---|---|
| $C_{max}$ (ng/mL) | 34.1 ± 38.9 | 25.6 ± 5.5 | 37.7 ± 16.5 |
| $T_{max}$ (hours) | 1.8 (0.5-6.0) | 1.8 (1.0-4.0) | 1.0 (0.3-2.0) |
| $t_{1/2}$ (hours) | 16.5 ± 2.4 | 26.1 ± 13.7 | 29.2 ± 25.3 |
| AUC (hr * ng/mL/mg) | 809 ± 923 | 736 ± 312 | 1,242 ± 1,129 |
| CL/F (L/hr) | 2.0 ± 0.9 | 1.6 ± 0.5 | 1.2 ± 0.6 |
| Vd/F (L) | 48.1 ± 23.4 | 51.0 ± 8.5 | 35.4 ± 12.4 |
| MRT (hours) | 24.9 ± 3.5 | 36.8 ± 18.9 | 41.7 ± 38.8 |

[a]$T_{max}$ values are expressed as median (range). All other values are expressed as mean ± SD and represent dose-adjusted pharmacokinetic parameters.
[b]Theacrine 25 mg
[c]Theacrine 125 mg
[d]Theacrine 125 mg + Caffeine 150 mg

TABLE 2

Caffeine Pharmacokinetics

| Parameter[a] | Condition 3[b] | Condition 4[c] |
|---|---|---|
| $C_{max}$ (ng/mL) | 33.4 ± 9.5 | 37.4 ± 11.8 |
| $T_{max}$ (hours) | 0.8 (0.5-1.5) | 1.0 (0.3-1.5) |
| $t_{1/2}$ (hours) | 6.2 ± 3.8 | 5.5 ± 2.2 |
| AUC (hr * ng/mL/mg) | 262.0 ± 74.1 | 323 ± 209 |
| CL/F (L/hr) | 4.1 ± 1.1 | 4.3 ± 2.0 |
| Vd/F (L) | 33.5 ± 13.7 | 30.2 ± 12.4 |
| MRT (hours) | 8.4 ± 4.3 | 8.0 ± 3.2 |

[a]$T_{max}$ values are expressed as median (range). All other values are expressed as mean ± SD and represent dose-adjusted parmocokinetic parameters.
[b]Caffeine 150 mg
[c]Theacrine 125 mg + Caffeine 150 mg

TABLE 3

Paraxanthine Pharmacokinetics

| Parameter[a] | Condition 3[b] | Condition 4[c] |
|---|---|---|
| $C_{max}$ (ng/mL) | 7.3 ± 1.5 | 8.4 ± 3.5 |
| $T_{max}$ (hours) | 5.0 (4.0-8.0) | 7.0 (1.5-8.0) |
| $t_{1/2}$ (hours) | 12.5 ± 12.7 | 14.8 ± 17.7 |
| AUC (hr * ng/mL/mg) | 174 ± 152 | 209 ± 202 |
| MRT (hours) | 19.1 ± 18.6 | 22.7 ± 26.2 |

Figure 12A:
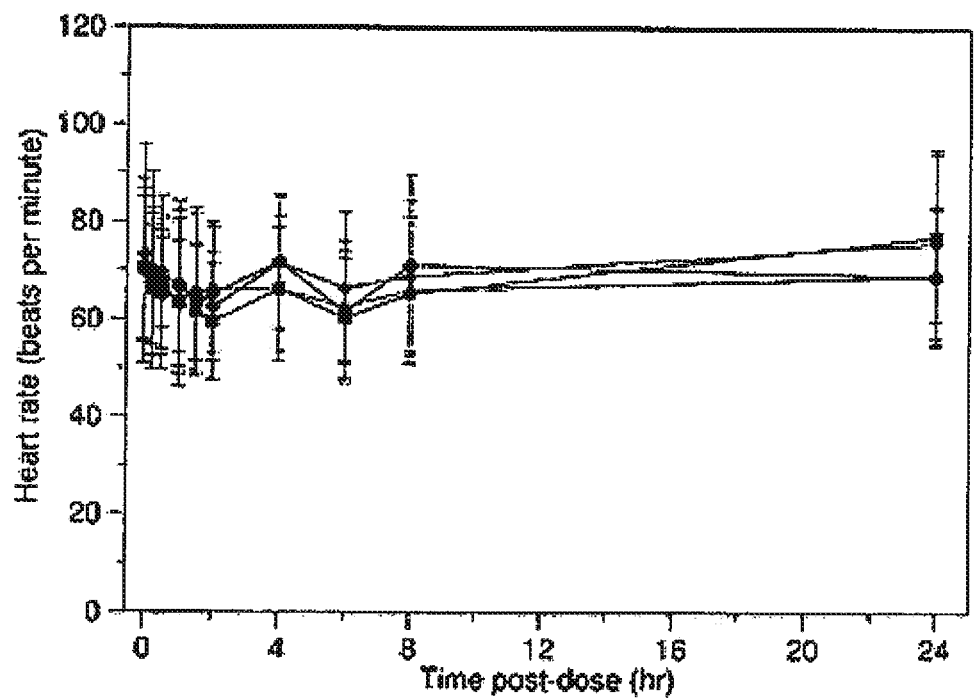
FIG. 12(A) depicts, in one embodiment, mean values in heart rate after single dose theacrine 25 mg (-●-) theacrine 125 mg (-■-), caffeine 150 mg (-♦-), or theacrine 125 mg plus caffeine 150 mg (-▲-).
Figure 12B:
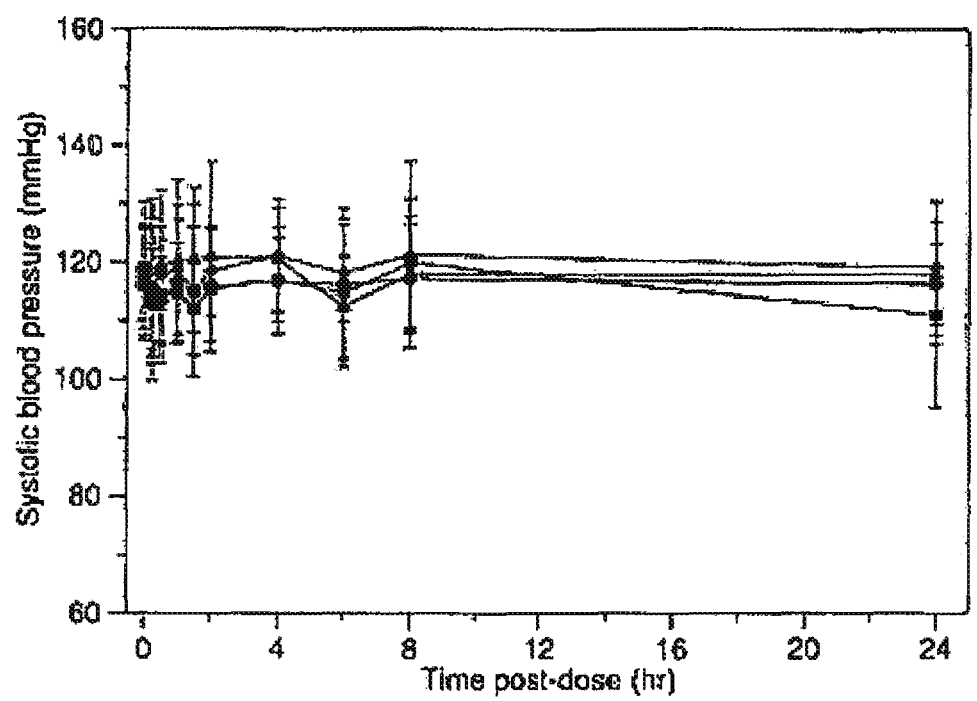
FIG. 12(B) depicts, in one embodiment, mean values in systolic blood pressure after single dose theacrine 25 mg (-●-) theacrine 125 mg (-■-) caffeine 150 mg (-♦-) or theacrine 125 mg plus caffeine 150 mg (-▲-).
Figure 12C:
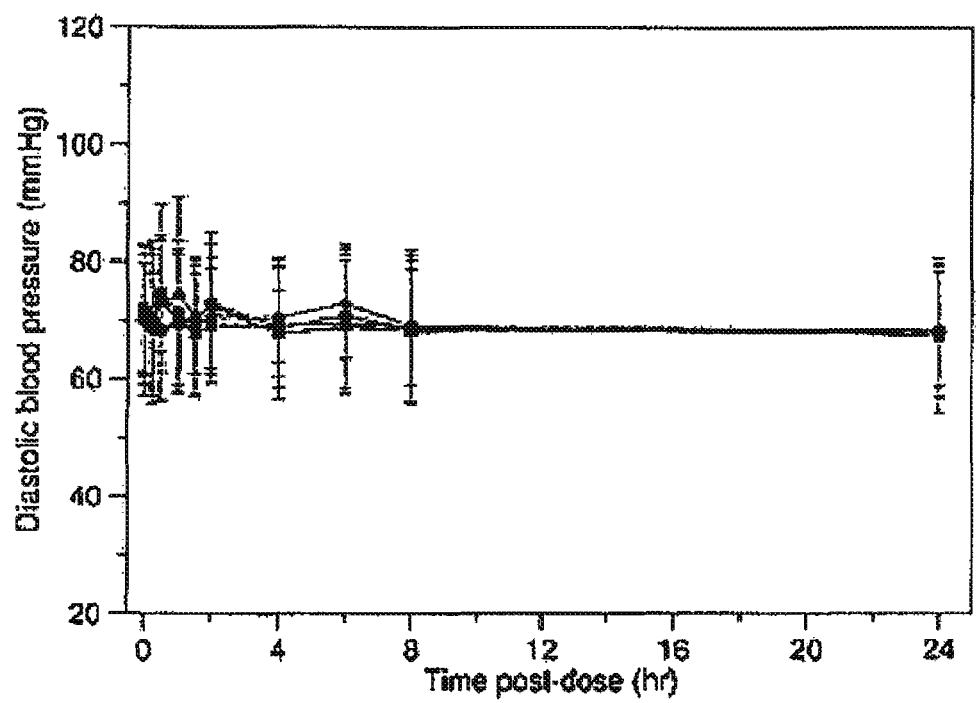
FIG. 12(C) depicts, in one embodiment, mean values in diastolic blood pressure after single dose theacrine 25 mg (-●-), theacrine 125 mg (-■-), caffeine 150 mg (-♦-), or theacrine 125 mg plus caffeine 150 mg (-▲-).
Figure 12D:
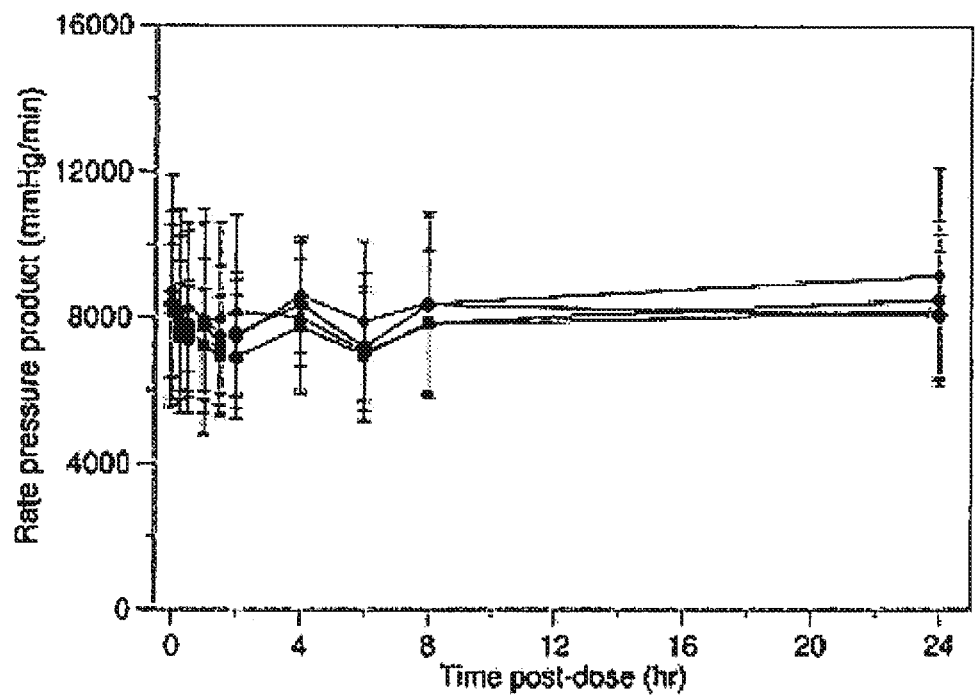
FIG. 12(D) depicts, in one embodiment, mean values in rate pressure product after single dose theacrine 25 mg (-●-) theacrine 125 mg (-■-) caffeine 150 mg (-◆-) or theacrine 125 mg plus caffeine 150 mg (-▲-).
Figure 13A:
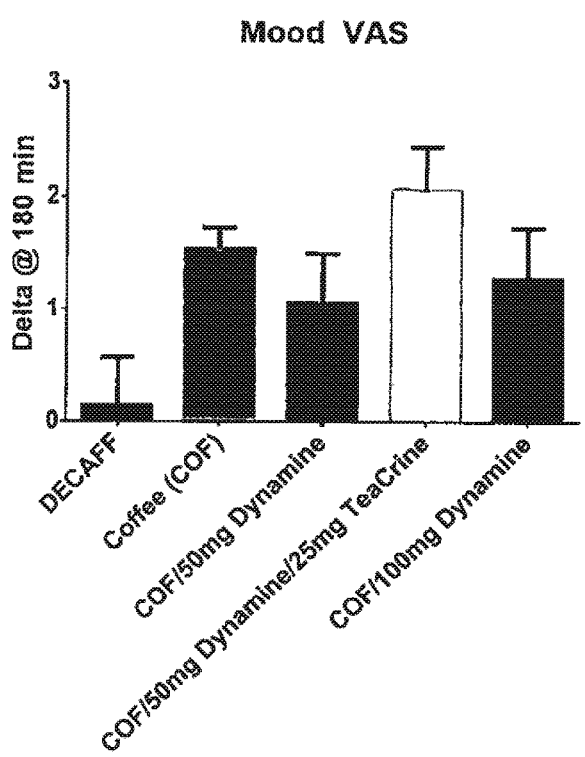
FIG. 13(A) depicts, in one embodiment, a graph of results of a trial showing the change (Delta) in perceived mood as measured using a VAS scale before and 180 minutes after consumption of a decaffeinated coffee beverage (DECAFF), caffeinated coffee (Coffee), Coffee with 50 mg methylliberine (Dynamine), Coffee with 50 mg Dynamine and 25 mg theacrine (TeaCrine), or Coffee with 100 mg Dynamine, as indicated.
Figure 13B:
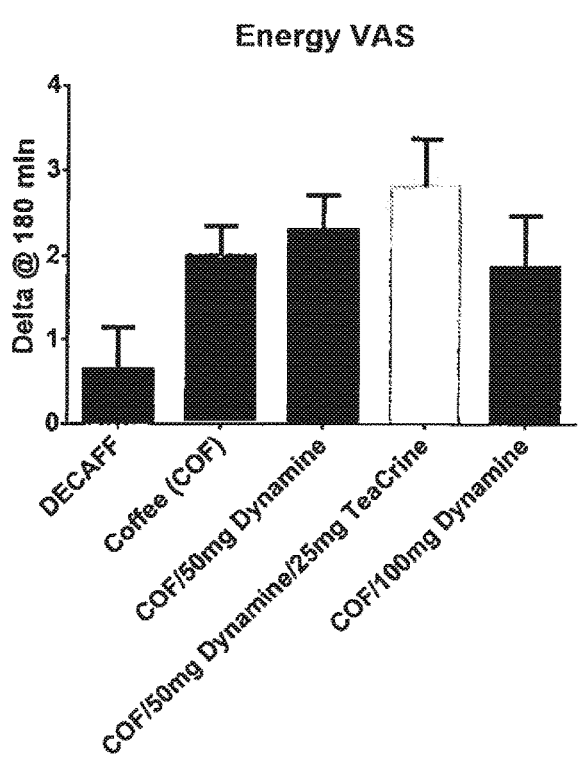
FIG. 13(B) depicts, in one embodiment, a graph of results of a trial showing the change (Delta) in perceived energy as measured using a VAS scale before and 180 minutes after consumption of a decaffeinated coffee beverage (DECAFF), caffeinated coffee (Coffee), Coffee with 50 mg methylliberine (Dynamine), Coffee with 50 mg Dynamine and 25 mg theacrine (TeaCrine), or Coffee with 100 mg Dynamine, as indicated.
Figure 13C:
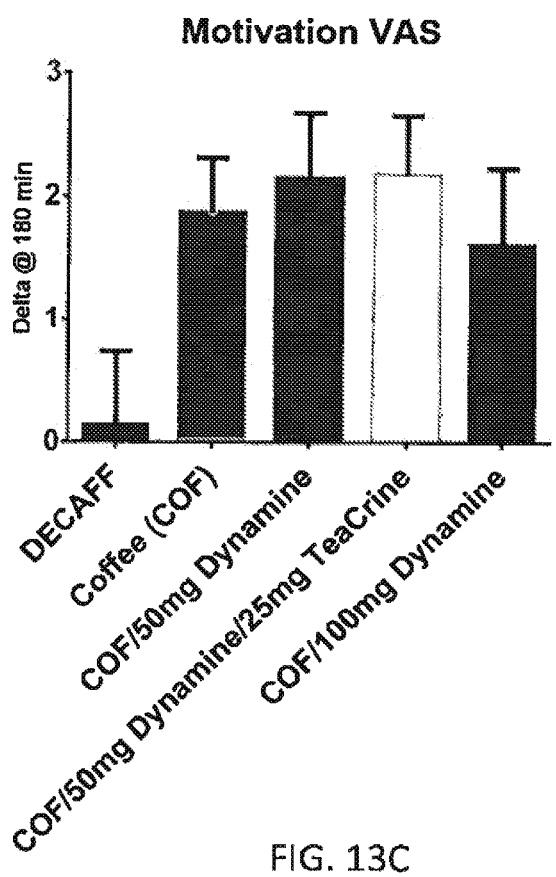
FIG. 13(C) depicts, in one embodiment, a graph of results of a trial showing the change (Delta) in perceived motivation as measured using a VAS scale before and 180 minutes after consumption of a decaffeinated coffee beverage (DECAFF), caffeinated coffee (Coffee), Coffee with 50 mg methylliberine (Dynamine), Coffee with 50 mg Dynamine and 25 mg theacrine (TeaCrine), or Coffee with 100 mg Dynamine, as indicated.
Figure 13D:
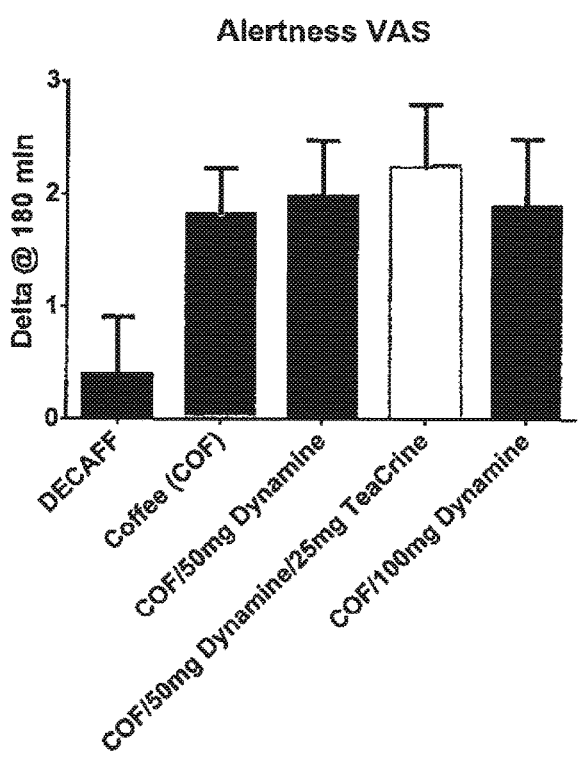
FIG. 13(D) depicts, in one embodiment, a graph of results of a trial showing the change (Delta) in perceived alertness as measured using a VAS scale before and 180 minutes after consumption of a decaffeinated coffee beverage (DECAFF), caffeinated coffee (Coffee), Coffee with 50 mg methylliberine (Dynamine), Coffee with 50 mg Dynamine and 25 mg theacrine (TeaCrine), or Coffee with 100 mg Dynamine, as indicated.
Figure 13E:
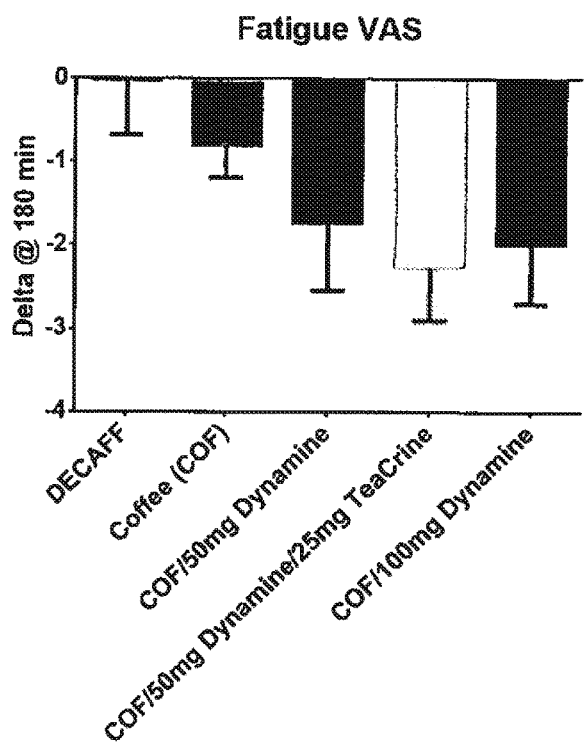
FIG. 13(E) depicts, in one embodiment, a graph of results of a trial showing the change (Delta) in perceived fatigue as measured using a VAS scale before and 180 minutes after consumption of a decaffeinated coffee beverage (DECAFF), caffeinated coffee (Coffee), Coffee with 50 mg methylliberine (Dynamine), Coffee with 50 mg Dynamine and 25 mg theacrine (TeaCrine), or Coffee with 100 mg Dynamine, as indicated.
Figure 13F:
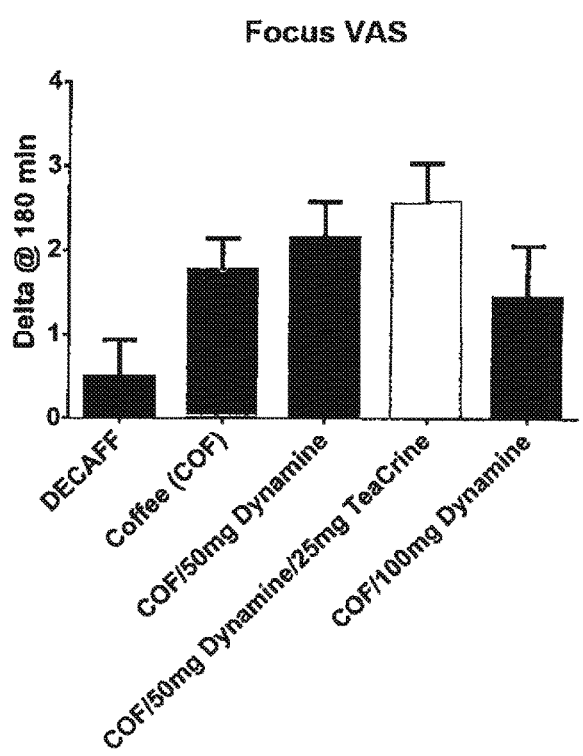
FIG. 13(F) depicts, in one embodiment, a graph of results of a trial showing the change (Delta) in perceived focus as measured using a VAS scale before and 180 minutes after consumption of a decaffeinated coffee beverage (DECAFF), caffeinated coffee (Coffee), Coffee with 50 mg methylliberine (Dynamine), Coffee with 50 mg Dynamine and 25 mg theacrine (TeaCrine), or Coffee with 100 mg Dynamine, as indicated.
Figure 13G:
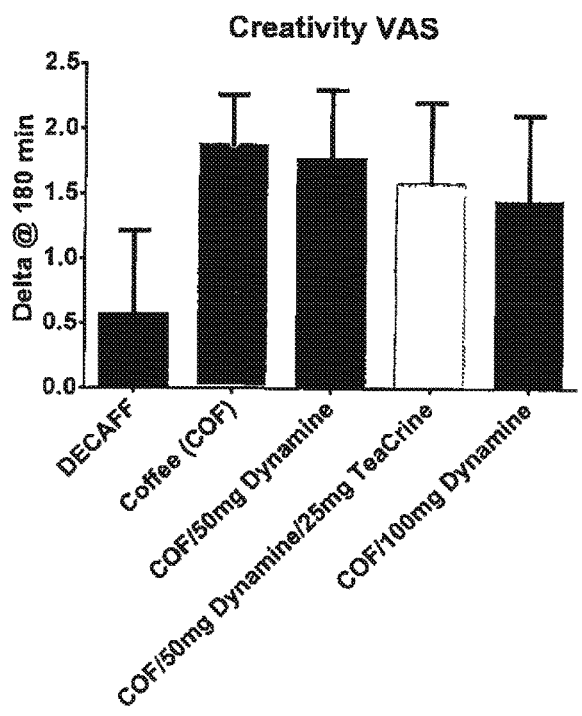
FIG. 13(G) depicts, in one embodiment, a graph of results of a trial showing the change (Delta) in perceived creativity as measured using a VAS scale before and 180 minutes after consumption of a decaffeinated coffee beverage (DECAFF), caffeinated coffee (Coffee), Coffee with 50 mg methylliberine (Dynamine), Coffee with 50 mg Dynamine and 25 mg theacrine (TeaCrine), or Coffee with 100 mg Dynamine, as indicated.
Figure 13H:
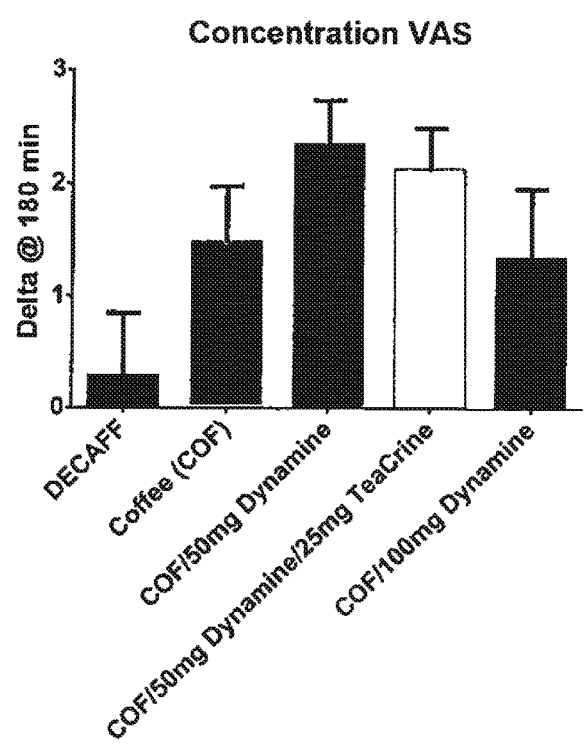
FIG. 13(H) depicts, in one embodiment, a graph of results of a trial showing the change (Delta) in perceived concentration as measured using a VAS scale before and 180 minutes after consumption of a decaffeinated coffee beverage (DECAFF), caffeinated coffee (Coffee), Coffee with 50 mg methylliberine (Dynamine), Coffee with 50 mg Dynamine and 25 mg theacrine (TeaCrine), or Coffee with 100 mg Dynamine, as indicated.
Figure 14A:
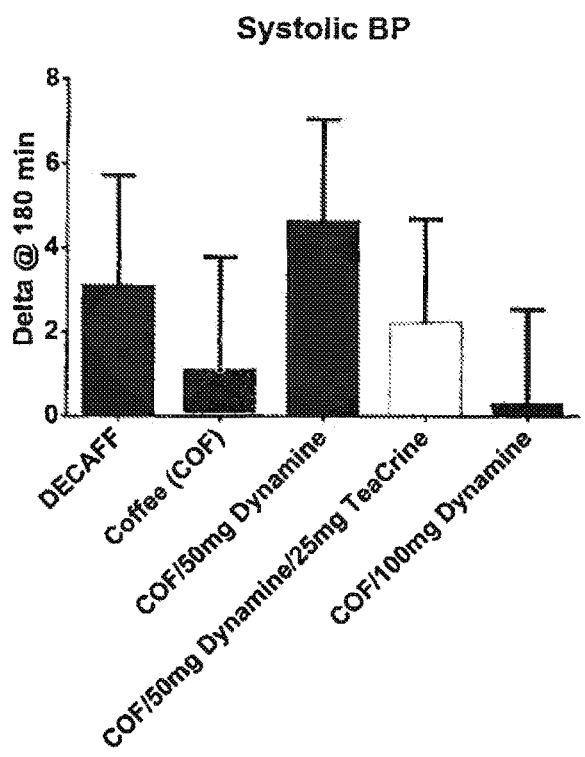
FIG. 14(A) depicts, in one embodiment, a graph of results of a trial showing the change (Delta) in mean values of systolic blood pressure (BP) before and 180 minutes after consumption of a decaffeinated coffee beverage (DECAFF), caffeinated coffee (Coffee), Coffee with 50 mg methylliberine (Dynamine), Coffee with 50 mg Dynamine and 25 mg theacrine (TeaCrine), or Coffee with 100 mg Dynamine, as indicated.
Figure 14B:
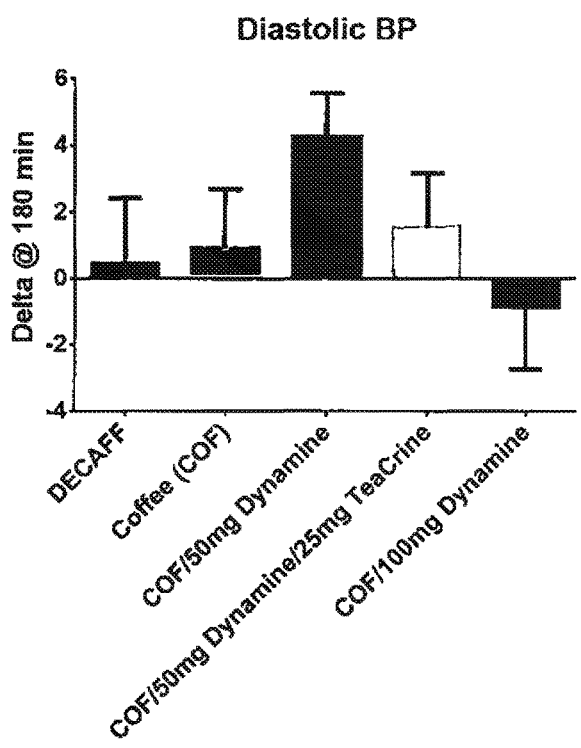
FIG. 14(B) depicts, in one embodiment, a graph of results of a trial showing the change (Delta) in mean values of diastolic blood pressure (BP) before and 180 minutes after consumption of a decaffeinated coffee beverage (DECAFF), caffeinated coffee (Coffee), Coffee with 50 mg methylliberine (Dynamine), Coffee with 50 mg Dynamine and 25 mg theacrine (TeaCrine), or Coffee with 100 mg Dynamine, as indicated.
Figure 14C:
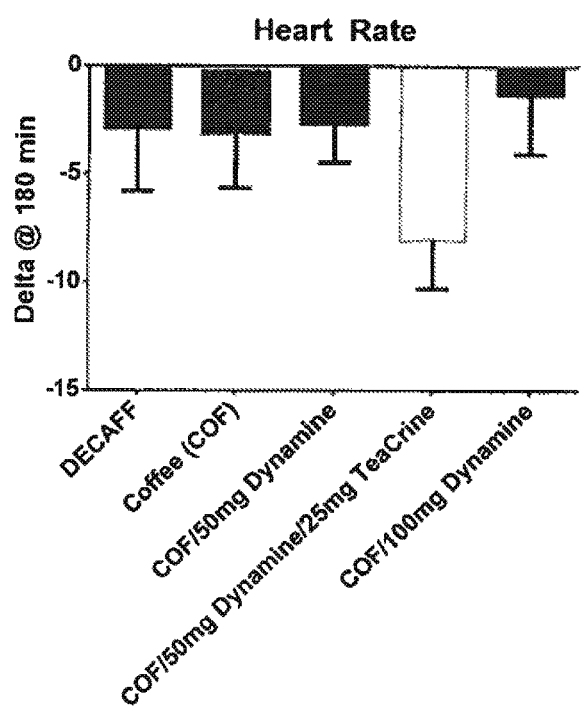
FIG. 14(C) in one embodiment, a graph of results of a trial showing the change (Delta) in mean values of heart rate before and 180 minutes after consumption of a decaffeinated coffee beverage (DECAFF), caffeinated coffee (Coffee), Coffee with 50 mg methylliberine (Dynamine), Coffee with 50 mg Dynamine and 25 mg theacrine (TeaCrine), or Coffee with 100 mg Dynamine, as indicated.
Figure 14D:
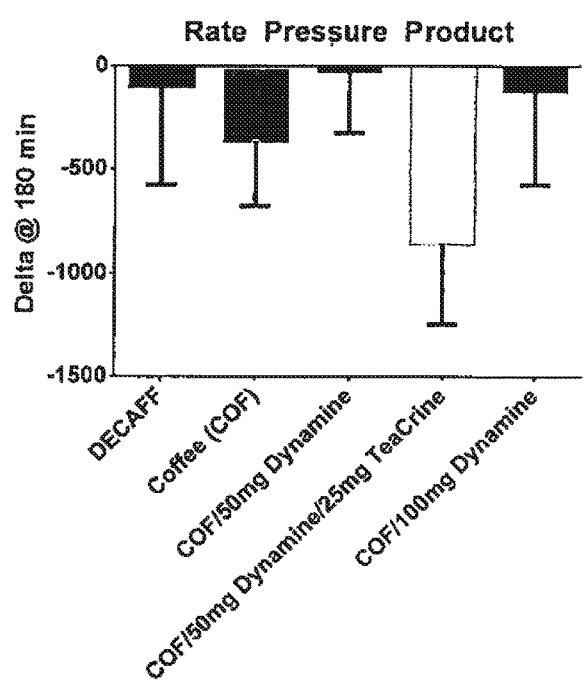
FIG. 14(D) in one embodiment, a graph of results of a trial showing the change (Delta) in mean values of rate pressure product before and 180 minutes after consumption of a decaffeinated coffee beverage (DECAFF), caffeinated coffee (Coffee), Coffee with 50 mg methylliberine (Dynamine), Coffee with 50 mg Dynamine and 25 mg theacrine (TeaCrine), or Coffee with 100 mg Dynamine, as indicated.
Figure 14E:
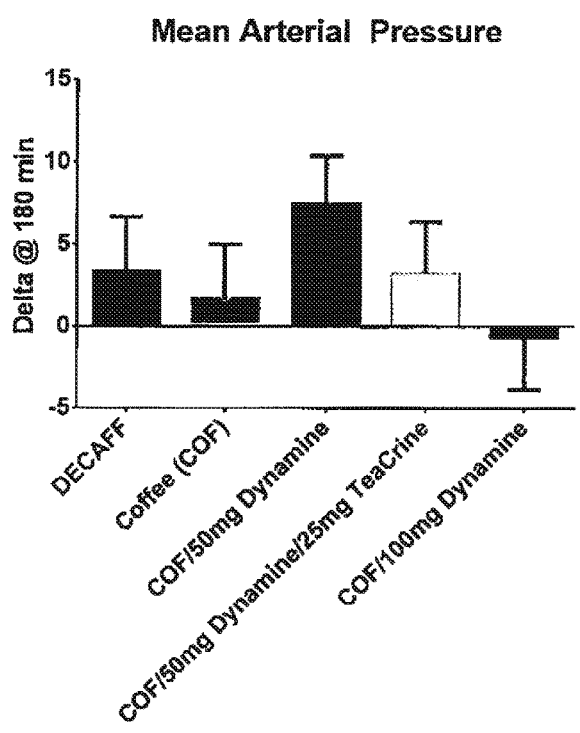
FIG. 14(E) in one embodiment, a graph of results of a trial showing the change (Delta) in mean values of mean arterial pressure before and 180 minutes after consumption of a decaffeinated coffee beverage (DECAFF), caffeinated coffee (Coffee), Coffee with 50 mg methylliberine (Dynamine), Coffee with 50 mg Dynamine and 25 mg theacrine (TeaCrine), or Coffee with 100 mg Dynamine, as indicated.
Figure 14F:
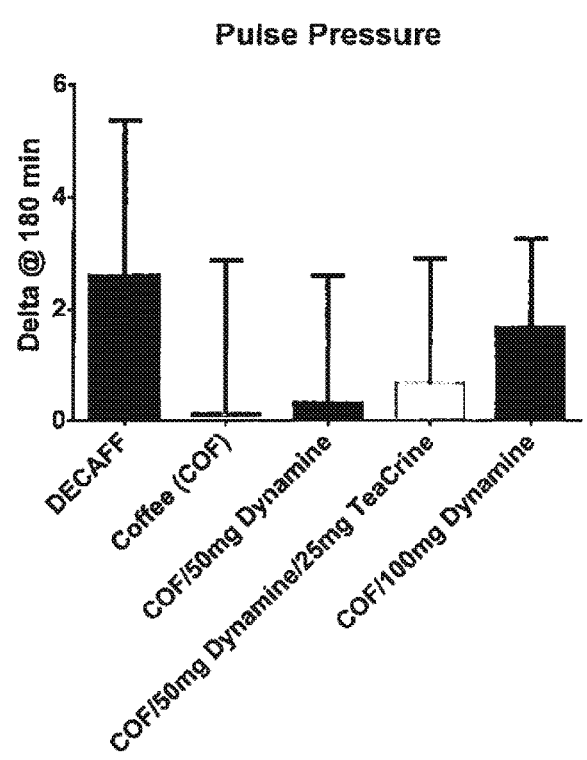
FIG. 14(F) in one embodiment, a graph of results of a trial showing the change (Delta) in mean values of pulse pressure before and 180 minutes after consumption of a decaffeinated coffee beverage (DECAFF), caffeinated coffee (Coffee), Coffee with 50 mg methylliberine (Dynamine), Coffee with 50 mg Dynamine and 25 mg theacrine (TeaCrine), or Coffee with 100 mg Dynamine, as indicated.

[a]$T_{max}$ values are expressed as median (range). All other values are expressed as mean ± SD and represent dose-adjusted pharmacokinetic parameters.
[b]Caffeine 150 mg
[c]Theacrine 125 mg + Caffeine 150 mg Pharmacodynamics. Hemodynamic parameters such as blood pressure and heart rate are elevated following co-administration of caffeine and other stimulants such as ephedrine. To determine the potential for a pharmacodynamics interaction between theacrine and caffeine, we evaluated systolic and diastolic blood pressure, heart rate, and rate pressure product following administration of both theacrine (25 mg and 125 mg) and caffeine (150 mg) alone and in combination (theacrine 125 mg plus caffeine 150 mg). Heart rate decreased slightly over the first two hours following administration for each of the four conditions returning to baseline by 24 hours post-ingestion (FIG. 12A). Systolic/diastolic blood pressure and rate pressure product remained relatively constant across the 24 hour evaluation period for each of the four conditions (FIGS. 12B, 12C, and 12D).

The experimental results reveal that the pharmacokinetics of theacrine, when ingested alone, were similar between the two doses tested. However, following co-ingestion with caffeine, theacrine disposition was significantly altered. Specifically, caffeine decreased theacrine's oral clearance (CL/F), which correlated with enhanced theacrine exposure parameters, area under the plasma concentration time curve (AUC) and maximum concentration ($C_{max}$). It is impossible to determine with certainty the exact mechanism for enhanced theacrine exposure, viz., decreased CL and/or increased oral bioavailability (F), in the absence of intravenous data. However, the finding that theacrine's elimination half-life ($t_{1/2}$ or Vd/CL) was unaffected by caffeine indicates that caffeine enhances theacrine's oral bioavailability (F), which is also consistent with the decreased oral volume of distribution (Vd/F) of theacrine. Theacrine had no impact on the pharmacokinetics of caffeine or paraxanthine, which is the primary caffeine metabolite in humans formed via CYP1A2-mediated 3-N-demethylation. Caffeine is completely absorbed following oral administration. Such results indicate that theacrine would not have a reciprocal effect on caffeine bioavailability. Determination of whether or not theacrine is a CYP1A2 substrate will provide further insight into caffeine's effect on theacrine disposition, viz., enhanced fraction absorbed and/or reduced first-pass hepatic metabolism.

One study subject was found to have exaggerated theacrine exposure in all treatment arms. It is unclear, however, whether the finding is genetic and/or environmental. The presence of a 5-methyl substituent and a carbamide at the 6-position distinguish theacrine from caffeine. Because theacrine contains a 3-methyl substituent, the primary site of caffeine metabolism via CYP1A2-mediated demethylation, it is possible that theacrine is also susceptible to CYP1A2-mediated metabolism. Caffeine exposure ($AUC_{0\text{-}\infty}$) is controlled by both environmental, as well as genetic factors. In particular, the CYP1A2 polymorphism (rs2470893), located in the common promoter region between CYPJA] and CYP1A2, significantly associated with caffeine exposure in non-smokers, but not in smokers. Non-smokers heterozygous or homozygous for the CYPJAI/CYP1A2 A allele had a significantly lower caffeine exposure compared to nullizygous individuals. Additional environmental factors including oral contraceptive use mask the effect of genetics on caffeine metabolism. The role of pharmacogenetics in theacrine pharmacokinetics and pharmacodynamics is of potential importance should CYP1A2 prove to be an important theacrine elimination pathway.

At the doses tested, the results reveal no effect on baseline hemodynamic parameters, e.g. heart rate and blood pressure, among the subjects receiving theacrine or caffeine administered alone or in combination. Such data are consistent with other studies demonstrating that theacrine supplementation (up to 400 mg/day for 8 weeks) appears to be safe in humans with no adverse effects on hemodynamic parameters. It is surprised to find that in repeat dose theacrine studies there is an absence of either sensitization or pharmacodynamic tolerance. Caffeine is a mixed $A_1/A_2$, adenosine receptor (AR) antagonist. It is believed that the acute psychostimulatory activity of caffeine is related to its ability to antagonize the $A_1AR$, which removes inhibition of the $A_{2A}$ AR leading to NMDA-dependent release of glutamate and dopamine. Following chronic caffeine administration, however, caffeine's primary effects shift from $A_1$-dependent to $A_{2A}$-dependent antagonism in tolerant individuals due to AAR desensitization. Administration of a cocktail containing both $A_1$ and $A_{2A}$ AR antagonists blocks theacrine stimulating activity in rats. However, simultaneous administration of $A_1$ and $A_{2A}$AR antagonists prevents the determination of individual contribution of $A_1$ and $A_{2A}$ AR to the pharmacologic effects of theacrine. These data present a hypothesis that theacrine has different $A_1$ and $A_{2A}$ binding affinities than caffeine, which permits discrimination between the A1 and A2A receptors at physiologically relevant concentrations. Theacrine's preferential reliance on $A_{2A}$ AR antagonism would provide a mechanistic basis for lack of pharmacodynamic tolerance. Overall, the experimental data suggest that the interactions between theacrine and adenosine receptors are complex.

Example 3. Improvements in Subjective Feelings, Cognitive Performance, and Hemodynamics In one clinical study, the effects of a single dose of theacrine, caffeine, or their combination on subjective feelings, cognitive performance, and hemodynamics in men and women were examined. In the study, 24 men and 26 women ingested a placebo, theacrine at 25 mg, theacrine at 125 mg, caffeine at 150 mg, or combination of 125 mg theacrine and 150 mg caffeine on five separate occasions, which were separated by approximately one week. Subjects rated their subjective feelings using a 10 cm visual analog scale at 30 minutes, 1, 2, 3, 4, and 5 hours post ingestion and performed the trail making test (TMT) of cognitive performance at baseline and at hours 2 and 4 post ingestion. Subjective feelings of attentiveness, sense of focus, and sense of energy improved with all active treatments. More favorable scores were generally associated with the caffeine and theacrine/caffeine combination treatments. Self-reported motivation to exercise significantly increased in caffeine and theacrine/caffeine combination treatments. Caffeine and theacrine/caffeine combination resulted in a significant increase in subjective focus from baseline to 2 hours post-ingestion, while the 125 mg theacrine treatment reached statistical significance at 3 hours post-ingestion. Motivation to exercise and sense of energy significantly increased from baseline to 2 hours post-ingestion in caffeine and theacrine/caffeine combination treatments. No condition effects were noted for the TMT ($p>0.05$), although a trend was present ($p=0.069$) for theacrine/caffeine combination treatment, with TMT time improved at 4 hours post ingestion compared to pre-ingestion. These findings indicate that theacrine, when used alone at 125 mg or in combination with caffeine, is safe and effective at improving subjective feelings related to energy in healthy men and women. Moreover, the data show that the combination of theacrine and caffeine may improve cognitive performance as assessed by the TMT.

Example 4. Improvements in Cognitive Performance

Another clinical study will demonstrate synergistic improvements in exercise performance and time to exhaustion obtained from 125 mg theacrine and 150 mg caffeine combination treatment over 275 mg caffeine or 275 theacrine administered alone. The purpose of this randomized, placebo-controlled, four-condition, double-blind clinical trial is to determine and compare the effects of theacrine to caffeine on various measures of cognitive performance under fatiguing conditions of a simulated athletic contest in high level male and female soccer players. Secondary purposes are to determine whether there is a synergistic effect of theacrine/caffeine combination as well as the impact on time-to-exhaustion in an "added time" scenario. After giving informed consent, 20 (males n=10, females n=10) Division I and professional soccer players will undergo baseline performance testing and then randomly assigned to order of supplementation of a placebo (P), caffeine (C), theacrine (T), and theacrine/caffeine combination (TC). In each condition, subjects will undergo a 15 minutes dynamic warm-up and then engage in a simulated soccer game on a high-speed treadmill. The "game" will be divided into two 45-minute halves. Simple, choice, and cognitive-load reaction time will be assessed immediately following each 45-minute half. After the second assessment, subjects will immediately be put back on the treadmill and asked to run to volitional fatigue at 90% VO2 max. The experimental results indicated that 125 mg theacrine/150 mg caffeine combined treatment outperformed 275 mg pure caffeine or 275 mg pure theacrine interventions. At almost half of the pure caffeine or pure theacrine dose, the combined theacrine/caffeine treatment resulted in a true synergistic and superior performance in comparison to the pure caffeine, the pure theacrine, or placebo group. More specifically, the combination of 125 mg theacrine/150 mg caffeine outperformed all other groups, including 275 mg pure caffeine, 275 mg of pure theacrine, and placebo, in measures of cognitive flexibility, attention and task switching, complex-choice reaction time and information processing.

Routes of Administration. The compounds may be administered by any route, including but not limited to oral, sublingual, buccal, ocular, pulmonary, rectal, and parenteral administration, or as an oral or nasal spray (e.g. inhalation of nebulized vapors, droplets, or solid particles). Parenteral administration includes, for example, intravenous, intramuscular, intraarterial, intraperitoneal, intranasal, intravaginal, intravesical (e.g., to the bladder), intradermal, transdermal, topical, or subcutaneous administration. Also contemplated within the scope of the invention is the instillation of theacrine in the body of the patient in a controlled formulation, with systemic or local release of the drug to occur at a later time. For example, the drug may be localized in a depot for controlled release to the circulation.

The pharmaceutical compositions of the present invention may be administered in combination with a pharmaceutically acceptable carrier. The active ingredients in such formulations may comprise from 1% by weight to 99% by weight, or alternatively, 0.1% by weight to 99.9% by weight. "Pharmaceutically acceptable carrier" means any carrier, diluent or excipient that is compatible with the other ingredients of the formulation and not deleterious to the user. Useful excipients include microcrystalline cellulose, magnesium stearate, calcium stearate, any acceptable sugar (e.g., mannitol, xylitol), and for cosmetic use an oil-base is preferred.

The nutraceutical compositions of the present invention may be administered in combination with a nutraceutically acceptable carrier. The active ingredients in such formulations may comprise from 1% by weight to 99% by weight, or alternatively, 0.1% by weight to 99.9% by weight. "Nutraceutically acceptable carrier" means any carrier, diluent or excipient that is compatible with the other ingredients of the formulation and not deleterious to the user. Useful excipients include microcrystalline cellulose, magnesium stearate, calcium stearate, any acceptable sugar (e.g., mannitol, xylitol), and for cosmetic use an oil-base is preferred.

Example 5. Enhanced Coffee Beverage Study

Summary of Enhance Coffee Beverage Study. With reference to FIGS. 13A-13H and 14A-14F, this study is a randomized, four-arm, within-subject crossover trial of N=12 apparently healthy male and female subjects to be recruited at a single investigational center in Northeast Ohio (i.e. The Center for Applied Health Sciences).

The volunteer subjects attended 5 study visits. At Visit 1, subjects were screened for participation (i.e., medical history, physical exam, routine blood work, background baseline diet). At Visits 2, 3, 4 and 5 subjects ingested four different kinds of coffee, and then fill out questionnaires that assess subjective changes in mood energy, fatigue, productivity, alertness, jittery, and focus.

Subjects were tested using Visual analogue scales (VAS) to assess subjective changes in mood, energy, fatigue, motivation, alertness, and focus. (FIGS. 13A-13H). In addition, the vitals of the subjects were tested. (FIGS. 14A-14F).

Description of Dataset. A blinded dataset of 15 cases was received on 06/03/20. All cases appeared to be complete with no missing data. One independent variable: Supplementation status was used in this study. This independent variable had three levels: A (decaffeinated coffee), B (caffeinated coffee) C (coffee with 50 mg methylliberine), D (coffee with 50 mg methylliberine and 25 mg theacrine), and E (coffee with 100 mg methylliberine). The decaffeinated coffee was 8 ounces of Tim Hortons medium roast. The brewed coffee was 8 ounces (8 oz) (236.59 mls) of Tim Hortons Original Blend, medium roast. All dependent variables assessed for all cases are outlined below along with an indication of when they were assessed. Vitals including systolic blood pressure, diabolic blood pressure, heart rate, rate pressure product, mean arterial pressure, and pulse pressure were also taken prior to the beverage (A, B, C, D, or E) consumption and at 60, 120, and 180 minutes after as set forth in Table 5. Assessments of VAS Mood, VAS Energy, VAS fatigue, VAS Motivation, VAS Alertness, VAS Focus, VAS Creativity, and VAS Concentration were assessed prior to the beverage (A, B, C, D, or E) consumption and at 60, 120, and 180 minutes after as set forth in Table 6. Comparisons of A, B, and C with D at 180 minutes were calculated as set forth in Table 7.

The provided dataset (Table 4) includes baseline screening data for age, body mass (in pounds and kilograms), height (in inches and centimeters), body mass index, systolic blood pressure, diastolic blood pressure, and heart rate for all study participants (Females, n=8; Males, n=7).

TABLE 4

Data of Volunteer Subjects

| | | Mean ± SD | Minimum | Maximum |
|---|---|---|---|---|
| Age | Female (n = 8) | 35.0 ± 8.9 | 21 | 44 |
| | Male (n = 7) | 28.8 ± 10.0 | 18 | 42 |
| | Total (n = 15) | 32.1 ± 9.6 | 18 | 44 |
| Weight (lbs) | Female | 150.2 ± 25.3 | 120 | 194 |
| | Male | 194.5 ± 48.1 | 144 | 280 |
| | Total | 170.9 ± 42.8 | 120 | 280 |
| Weight (kg) | Female | 68.1 ± 11.6 | 54 | 88 |
| | Male | 88.2 ± 21.8 | 66 | 127 |
| | Total | 77.5 ± 19.5 | 54 | 127 |
| Height (inches) | Female | 66.0 ± 3.2 | 60 | 69 |
| | Male | 70.4 ± 2.9 | 67 | 75 |
| | Total | 68.1 ± 3.7 | 60 | 75 |
| Height (cm) | Female | 167.7 ± 8.0 | 152.4 | 175.3 |
| | Male | 178.9 ± 7.5 | 170.2 | 190.5 |
| | Total | 172.9 ± 9.5 | 152.4 | 190.5 |
| Body Mass Index ($kg/m^2$) | Female | 24.3 ± 2.2 | 22 | 28.6 |
| | Male | 27.3 ± 4.8 | 20 | 34.8 |
| | Total | 25.7 ± 3.8 | 20 | 34.8 |
| Systolic Blood Pressure (mm Hg) | Female | 120.0 ± 5.7 | 112 | 127 |
| | Male | 123.4 ± 11.0 | 108 | 136 |
| | Total | 121.6 ± 8.4 | 108 | 136 |
| Diastolic Blood Pressure (mm Hg) | Female | 75.5 ± 8.7 | 67 | 90 |
| | Male | 75.3 ± 6.4 | 67 | 86 |
| | Total | 75.4 ± 7.5 | 67 | 90 |
| Heart Rate (bpm) | Female | 79.4 ± 13.8 | 53 | 98 |
| | Male | 74.6 ± 13.4 | 50 | 90 |
| | Total | 77.1 ± 13.3 | 50 | 98 |

TABLE 5

Hemodynamic Variables.
Hemodynamic Variables

| Variables | Pre | 60 min | 120 min | 180 min | Delta (180 − Pre) | p-value (W 8-W 0) | Condition | Time | Cond × Time |
|---|---|---|---|---|---|---|---|---|---|
| Systolic Blood Pressure (mm Hg) | | | | | | | | | |
| A | 116.1 ± 12.3 | 116.7 ± 12.5 | 119.1 ± 10.2 | 119.1 ± 11.2 | 3.1 ± 10.3 | 0.44 | 0.16 | 0.09 | 0.36 |
| B | 117.6 ± 12.6 | 113.7 ± 11.1 | 115.1 ± 10.3 | 118.7 ± 8.3 | 1.1 ± 10.5 | 0.17 | | | |
| C | 117.7 ± 11.0 | 117.7 ± 9.5 | 123.6 ± 11.2 | 122.3 ± 10.2 | 4.6 ± 9.5 | 0.02 | | | |
| D | 119.5 ± 10.4 | 121.3 ± 8.4 | 121.3 ± 10.4 | 113.3 ± 6.9 | 2.2 ± 9.6 | 0.66 | | | |
| E | 118.8 ± 11.5 | 118.9 ± 10.8 | 120.0 ± 13.5 | 119.1 ± 8.2 | 0.3 ± 8.8 | 0.95 | | | |
| Diastolic Blood Pressure (mm Hg) | | | | | | | | | |
| A | 77.3 ± 7.1 | 75.8 ± 9.8 | 76.3 ± 8.3 | 77.8 ± 8.4 | 0.5 ± 7.6 | 0.58 | 0.02 | 0.53 | 0.04 |
| B | 76.0 ± 8.3 | 76.1 ± 8.9 | 76.2 ± 8.7 | 76.9 ± 8.2 | 0.9 ± 6.9 | 0.95 | | | |
| C | 78.1 ± 9.4 | 78.5 ± 8.4 | 82.0 ± 7.7 | 82.3 ± 6.4 | 4.3 ± 5.1 | 0.003 | | | |
| D | 77.5 ± 7.2 | 80.9 ± 8.1 | 79.0 ± 5.9 | 79.0 ± 6.5 | 1.5 ± 6.4 | 0.17 | | | |
| E | 76.7 ± 9.3 | 78.4 ± 7.1 | 75.9 ± 7.1 | 75.3 ± 8.9 | −1.4 ± 6.7 | 0.27 | | | |

TABLE 5-continued

Hemodynamic Variables.
Hemodynamic Variables

| Variables | Pre | 60 min | 120 min | 180 min | Delta (180 − Pre) | Within-Group p-value (W 8-W 0) | Condition | Time | Cond × Time |
|---|---|---|---|---|---|---|---|---|---|
| | | | | Heart Rate (beats/min) | | | | | |
| A | 74.5 ± 13.0 | 70.7 ± 14.6 | 70.5 ± 14.9 | 71.7 ± 15.8 | −2.9 ± 11.3 | 0.18 | 0.35 | 0.005 | 0.45 |
| B | 74.8 ± 12.9 | 70.7 ± 13.4 | 67.9 ± 13.4 | 71.7 ± 14.5 | −3.1 ± 9.7 | 0.04 | | | |
| C | 75.1 ± 12.8 | 72.3 ± 12.6 | 69.7 ± 13.0 | 72.4 ± 11.8 | −2.7 ± 7.0 | 0.02 | | | |
| D | 74.5 ± 12.4 | 68.3 ± 12.3 | 69.5 ± 12.3 | 66.5 ± 13.2 | −8.0 ± 8.8 | 0.005 | | | |
| E | 73.8 ± 11.9 | 71.1 ± 11.0 | 70.5 ± 17.2 | 72.5 ± 15.1 | −1.3 ± 10.7 | 0.54 | | | |
| | | | | Rate Pressure Product | | | | | |
| A | 86.9 ± 19.6 | 83.1 ± 20.3 | 84.4 ± 20.1 | 85.9 ± 21.7 | −1.0 ± 0.2 | 0.53 | 0.31 | 0.07 | 0.52 |
| B | 88.2 ± 19.1 | 80.2 ± 16.0 | 78.1 ± 17.3 | 84.6 ± 15.8 | −3.6 ± 12.1 | 0.004 | | | |
| C | 88.7 ± 18.5 | 85.3 ± 17.6 | 86.2 ± 17.9 | 88.4 ± 15.1 | −0.3 ± 11.5 | 0.57 | | | |
| D | 89.3 ± 18.9 | 82.6 ± 14.3 | 83.0 ± 15.8 | 80.7 ± 16.1 | −8.6 ± 15.1 | 0.04 | | | |
| E | 87.8 ± 17.1 | 84.9 ± 17.7 | 85.6 ± 25.6 | 86.6 ± 19.9 | −1.2 ± 17.4 | 0.90 | | | |
| | | | | Mean Arterial Pressure | | | | | |
| A | 167.6 ± 14.8 | 167.3 ± 17.7 | 170.0 ± 13.4 | 171.0 ± 15.5 | 3.4 ± 12.7 | 0.45 | 0.05 | 0.08 | 0.15 |
| B | 168.3 ± 16.3 | 164.4 ± 15.9 | 165.9 ± 14.0 | 170.0 ± 11.0 | 1.7 ± 12.7 | 0.28 | | | |
| C | 169.8 ± 15.6 | 170.0 ± 13.5 | 178.3 ± 14.3 | 177.2 ± 12.1 | 7.4 ± 11.2 | 0.004 | | | |
| D | 171.2 ± 14.1 | 175.2 ± 12.1 | 172.0 ± 8.6 | 174.4 ± 7.9 | 3.2 ± 12.2 | 0.48 | | | |
| E | 170.0 ± 15.8 | 171.1 ± 13.9 | 170.6 ± 17.8 | 169.3 ± 12.8 | −0.67 ± 12.4 | 0.93 | | | |
| | | | | Pulse Pressure | | | | | |
| A | 38.7 ± 11.6 | 40.9 ± 9.0 | 42.9 ± 10.4 | 41.3 ± 8.3 | 2.6 ± 10.8 | 0.51 | 0.53 | 0.32 | 0.64 |
| B | 41.6 ± 10.8 | 37.7 ± 7.8 | 38.9 ± 9.9 | 41.7 ± 10.3 | 0.1 ± 10.6 | 0.27 | | | |

TABLE 6

VAS Assessments
Visual Analog Scales

| Variables | Pre | 60 min | 120 min | 180 min | Delta (180 − Pre) | Within-Group p-value (W 8-W 0) | Condition | Time | Cond × Time |
|---|---|---|---|---|---|---|---|---|---|
| | | | | Mood | | | | | |
| A | 5.8 ± 1.8 | 6.2 ± 1.5 | 6.1 ± 2.1 | 5.9 ± 2.4 | 0.14 ± 1.65 | 0.57 | 0.19 | <0.001 | 0.02 |
| B | 5.4 ± 2.0 | 6.6 ± 1.7 | 6.6 ± 1.5 | 6.9 ± 1.6 | 1.54 ± 0.73 | <0.001 | | | |
| C | 6.2 ± 1.5 | 6.6 ± 1.3 | 7.0 ± 1.8 | 7.2 ± 1.8 | 1.05 ± 1.72 | 0.05 | | | |
| D | 5.2 ± 1.8 | 6.2 ± 1.5 | 6.9 ± 1.2 | 7.3 ± 1.6 | 2.05 ± 1.49 | <0.001 | | | |
| E | 5.6 ± 1.6 | 6.6 ± 1.7 | 6.7 ± 1.5 | 6.9 ± 2.0 | 1.27 ± 1.76 | 0.006 | | | |
| | | | | Energy | | | | | |
| A | 4.9 ± 1.7 | 5.9 ± 1.6 | 5.7 ± 2.1 | 5.6 ± 2.3 | 0.64 ± 2.00 | 0.09 | 0.24 | <0.001 | 0.01 |
| B | 4.5 ± 1.4 | 6 5 ± 1.6 | 6.5 ± 1.5 | 6.5 ± 1.4 | 2.00 ± 1.35 | <0.001 | | | |
| C | 4.9 ± 1.9 | 6.5 ± 1.6 | 6.9 ± 1.7 | 7.2 ± 1.5 | 2.31 ± 1.60 | <0.001 | | | |
| D | 4.0 ± 2.1 | 6.4 ± 1.5 | 6.9 ± 1.3 | 6.8 ± 1.7 | 2.83 ± 2.15 | <0.001 | | | |
| E | 4.5 ± 1.7 | 6.0 ± 1.7 | 6.7 ± 1.7 | 6.4 ± 1.9 | 1.87 ± 2.36 | <0.001 | | | |
| | | | | Fatigue | | | | | |
| A | 3.8 ± 2.1 | 3.8 ± 2.0 | 3.5 ± 2.1 | 3.8 ± 2.4 | 0.00 ± 2.60 | 0.93 | 0.44 | <0.001 | 0.09 |
| B | 4.6 ± 2.3 | 2.8 ± 2.0 | 3.1 ± 2.0 | 3.8 ± 2.1 | −0.80 ± 1.51 | 0.001 | | | |
| C | 4.3 ± 2.3 | 2.5 ± 1.4 | 2.7 ± 2.3 | 2.6 ± 2.0 | −1.73 ± 3.11 | 0.01 | | | |
| D | 4.5 ± 2.4 | 3.1 ± 1.8 | 2.3 ± 1.8 | 2.3 ± 1.8 | −2.27 ± 2.41 | <0.001 | | | |
| E | 4.6 ± 1.9 | 3.0 ± 1.9 | 3.0 ± 2.0 | 2.6 ± 2.4 | −1.99 ± 2.76 | 0.005 | | | |
| | | | | Motivation | | | | | |
| A | 5.2 ± 2.1 | 5.9 ± 1.7 | 5.2 ± 2.2 | 5.3 ± 2.3 | 0.14 ± 2.31 | 0.45 | 0.40 | <0.001 | 0.03 |
| B | 4.3 ± 1.6 | 6.2 ± 1.5 | 6.2 ± 1.5 | 6.2 ± 1.7 | 1.87 ± 1.71 | <0.001 | | | |
| C | 4.8 ± 2.2 | 6.3 ± 1.6 | 6.6 ± 2.3 | 6.9 ± 2.2 | 2.15 ± 2.04 | <0.001 | | | |
| D | 4.4 ± 1.9 | 6.4 ± 1.6 | 6.3 ± 1.7 | 6.6 ± 2.0 | 2.17 ± 1.85 | <0.001 | | | |
| E | 4.9 ± 2.1 | 6.1 ± 1.8 | 6.6 ± 1.8 | 6.5 ± 2.1 | 1.61 ± 2.41 | 0.003 | | | |
| | | | | Alertness | | | | | |
| A | 5.4 ± 1.7 | 5.9 ± 1.7 | 6.1 ± 2.2 | 5.8 ± 2.2 | 0.39 ± 1.99 | 0.22 | 0.19 | <0.001 | 0.08 |
| B | 4.5 ± 1.5 | 6.6 ± 1.3 | 6.5 ± 1.4 | 6.3 ± 1.7 | 1.83 ± 1.56 | <0.001 | | | |

TABLE 6-continued

VAS Assessments
Visual Analog Scales

| | | | | | Within-Group | | | | |
|---|---|---|---|---|---|---|---|---|---|
| Variables | Pre | 60 min | 120 min | 180 min | Delta (180 − Pre) | p-value (W 8-W 0) | Condition | Time | Cond × Time |
| C | 5.1 ± 1.9 | 6.7 ± 1.3 | 7.3 ± 1.5 | 7.1 ± 1.9 | 1.98 ± 1.91 | <0.001 | | | |
| D | 4.6 ± 2.3 | 6.6 ± 1.5 | 6.9 ± 1.4 | 6.9 ± 1.9 | 2.23 ± 2.17 | <0.001 | | | |
| E | 5.1 ± 2.0 | 6.6 ± 1.4 | 6.9 ± 1.5 | 6.9 ± 1.9 | 1.89 ± 2.32 | <0.001 | | | |

TABLE 7

Comparative Analysis of Groups A, B, and C with D. Hemodynamic
Between-Group Comparisons - Delta @ 180 minutes.

| Variable | Compared Groups | Mean Difference | 95% CI | p-value | Effect Size (d) | % Change |
|---|---|---|---|---|---|---|
| Systolic Blood | D vs. A | −0.87 ± 3.1 | (−7.5, 5.8) | 0.78 | −0.08 | −0.8 |
| Pressure | D vs. B | 1.13 ± 3.8 | (−7.0, 9.3) | 0.77 | 0.12 | 0.9 |
| (mm Hg) | D vs. C | −2.40 ± 2.8 | (−8.4, 3.6) | 0.40 | 0.04 | 0.3 |
| Diastolic Blood | D vs. A | 1.07 ± 2.3 | (−3.8, 6.0) | 0.65 | −0.15 | −1.6 |
| Pressure | D vs. B | 0.60 ± 2.4 | (−4.5, 5.7) | 0.81 | −0.20 | −2.2 |
| (mm Hg) | D vs. C** | −2.73 ± 1.5** | (5.9, 0.4) ** | 0.08** | −0.61** | −6.4** |
| Heart Rate | D vs. A | −5.1 ± 3.1 | (−5.1, 3.1) | 0.12 | −0.38 | −6.9 |
| (beats/min) | D vs. B** | −4.9 ± 2.6** | (−4.9, 2.6) ** | 0.08** | −0.37** | −6.6** |
| | D vs. C# | −5.3 ± 2.3# | (−5.3, 2.3)# | 0.04# | −0.42# | −7.2# |
| Rate | D vs. A** | −7.6 ± 4.2** | (−16.7, 1.5) ** | 0.10** | −0.40** | −8.5** |
| Pressure | D vs. B | −4.9 ± 4.1 | (−13.8, 4.0) | 0.25 | −0.28 | −5.5 |
| Product | D vs. C# | −8.3 ± 3.1# | (−14.9, 1.7) # | 0.02# | −0.48# | −9.3# |
| Mean Arterial | D vs. A | −0.16 ± 3.8 | (−8.3, 8.0) | 0.97 | −0.01 | −0.1 |
| Pressure | D vs. B | 1.53 ± 4.9 | (−9.0, 12.1) | 0.76 | 0.12 | 0.9 |
| (mm Hg) | D vs. C | −4.22 ± 3.3 | (−11.2, 2.8) | 0.22 | −0.33 | −2.5 |
| Pulse | D vs. A | −1.9 ± 3.3 | (−9.0, 5.2) | 0.57 | −0.21 | −5.1 |
| Pressure | D vs. B | 0.5 ± 3.5 | (−6.1, 7.1) | 0.87 | 0.06 | 1.3 |
| (mm Hg) | D vs. C | 0.3 ± 2.6 | (−5.3, 6.0) | 0.90 | 0.04 | 0.7 |

Summary of Statics for Enhance Coffee Study (Example 5). A significant level of 0.05 was used for all statistical determinations and a p-value from 0.05-0.10 was deemed a trend or tendency. Normality of the frequency distributions were assessed using the Shapiro-Wilk test. Nearly all variables were confirmed to have a normal distribution. Due to the repeated nature of the study design, the variables who were found to be non-normal were not transformed and a traditional parametric approach to statistical analysis was employed. 5×4 mixed factorial ANOVAs were completed to assess condition, time, and condition × time interaction effects. LSD post-hoc procedures were used to assess individual comparisons between groups. In all instances where the sphericity assumption was not met, the Greenhouse-Geiser correction was applied. All statistically significant outcomes are denoted with #, while all statistical tendencies or trends are denoted with **.

Whereas, the present invention has been described in relation to certain embodiments thereof, and many details have been put forth in its illustration, it should be understood that other and further modifications, apart from those shown or suggested herein, may be made within the spirit and scope of this invention. Descriptions of the embodiments shown in the drawings should not be construed as limiting or defining the ordinary and plain meanings of the terms of the claims unless such is explicitly indicated.

As such, those skilled in the art will appreciate that the conception, upon which this disclosure is based, may readily be utilized as a basis for the designing of other structures, methods and system for carrying out the several purposes of the present invention. It is important, therefore, that the claims be regarded as including such equivalent constructions insofar as they do not depart from the spirit and scope of the present invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

What is claimed is:

1. A caffeinated beverage composition supplemented with methylliberine and theacrine, the composition comprising:
    a caffeinated drink having a caffeine content of between about 1 mg/oz to 65 mg/oz;
    theacrine in an amount of between about 1.5 mg/oz to 15 mg/oz; and
    methylliberine in an amount of between about 3.0 mg/oz to 30 mg/oz.

2. The composition of claim 1, wherein the theacrine and the methylliberine are present in a weight ratio of between about 1:1.5 to 1:2.75.

3. The composition of claim 1, wherein the caffeine content is from 10 mg/oz to 30 mg/oz.

4. The composition of claim 1, wherein the caffeinated drink is brewed coffee.

5. The composition of claim 1, wherein the caffeinated drink is brewed coffee and the theacrine and the methylliberine are present in a weight ratio of between about 1:1.5 to 1:2.75.

6. The composition of claim 5, wherein the brewed coffee is a non-espresso brew having a caffeine content of between about 10 mg/oz to 30 mg/oz.

7. The composition of claim 5, wherein the brewed coffee is an espresso brew having a caffeine content of between about 30 mg/oz to 65 mg/oz in not more than 3 ounce volume.

8. The composition of claim 1, wherein the caffeinated drink is a coffee drink, a tea, an energy drink, or a cola.

9. The composition of claim 8, wherein the caffeinated drink is a tea and the tea is black or green tea.

10. The composition of claim 1, wherein the caffeinated beverage upon consumption by a person, increases mood, energy, alertness, motivation, and/or focus in the person compared to the caffeinated beverage alone or the caffeinated beverage supplemented only with methylliberine of between about 6 mg/oz or 12.5 mg/oz.

11. The composition of claim 10, wherein the caffeinated beverage does not adversely affect heart rate and/or blood pressure in the person.

12. The composition of claim 10, wherein the increased mood, energy, alertness, motivation, and/or focus in the person is experienced by the person up to about 5 hours after consumption.

13. A method of preparing an enhanced caffeinated beverage, comprising: adding theacrine and methylliberine to a caffeinated drink, wherein the theacrine is added in an amount of between about 1.5 mg/oz to 15 mg/oz and the methylliberine is added in an amount of between about 3.0 mg/oz to 30 mg/oz.

14. The method of claim 13, wherein the caffeinated drink has a caffeine content of between about 1 mg/oz to 65 mg/oz.

15. The method of claim 14, wherein the theacrine and the methylliberine are added in a weight ratio of between about 1:1.5 to 1:2.75.

16. The method of claim 13, wherein the caffeinated drink is selected from a group consisting of a brewed coffee, a tea, an energy drink, or a cola.

17. The method of claim 13, wherein the caffeinated drink is a brewed coffee and the theacrine and methylliberine are added to coffee grounds prior to brewing the brewed coffee or the theacrine and methylliberine are added to the brewed coffee.

18. The method of claim 17, wherein the brewed coffee is a non-espresso or espresso brewed coffee.

19. The method of claim 17, wherein the brewed coffee is a hot brewed coffee or a cold brewed coffee.

20. A coffee beverage composition supplemented with methylliberine and theacrine, the composition comprising:
a coffee drink having a caffeine content of between about 1 mg/oz to 65 mg/oz;
theacrine in an amount of between about 1.5 mg/oz to 15 mg/oz; and
methylliberine in an amount of between about 3.0 mg/oz to 30 mg/oz, and wherein the theacrine and the methylliberine are in a weight ratio of between about 1:1.5 to 1:2.75.

* * * * *